(12) United States Patent
Nolan et al.

(10) Patent No.: US 7,767,841 B1
(45) Date of Patent: Aug. 3, 2010

(54) GOLD COMPLEXES FOR CATALYSIS AND PREPARATION THEREOF

(75) Inventors: Steven P. Nolan, Tarragona (ES); Pierre de Fremont, Tarragona (ES)

(73) Assignee: University of New Orleans Research and Technology Foundation, Inc., New Orleans, LA (US)

(*) Notice: Subject to any disclaimer, the term of this patent is extended or adjusted under 35 U.S.C. 154(b) by 0 days.

(21) Appl. No.: 12/098,863

(22) Filed: Apr. 7, 2008

Related U.S. Application Data

(60) Provisional application No. 60/910,385, filed on Apr. 5, 2007.

(51) Int. Cl.
*C07F 1/12* (2006.01)
*C01F 1/00* (2006.01)

(52) U.S. Cl. .................................................. 556/112
(58) Field of Classification Search ................. 556/112
See application file for complete search history.

(56) References Cited

OTHER PUBLICATIONS

Böhler et al., New J. Chem., vol. 26, pp. 1291-1295 (2002).*

* cited by examiner

*Primary Examiner*—Porfirio Nazario Gonzalez
(74) *Attorney, Agent, or Firm*—Garvey, Smith, Nehrbass & North, L.L.C.; Seth M. Nehrbass; Vanessa M. D'Souza

(57) ABSTRACT

A number of cationic gold(I) and neutral gold(III) complexes have been synthesized and found to be stabilized by the use of N-heterocyclic carbene ligands. These species are often employed as in situ-generated reactive intermediates in gold catalyzed organic transformations. An isolated, well-defined cationic species was tested in gold mediated carbene transfer reactions from ethyl diazoacetate.

8 Claims, 6 Drawing Sheets

(IPr)AuCl (1)

(IMes)AuCl (2)

(SIPr)AuCl (3)

(SIMes)AuCl (4)

(ICy)AuCl (4)

(IAd)AuCl (5)

(I$^t$Bu)AuCl (7)

(NHC)Au(I)Cl complexes used as starting material in this study.

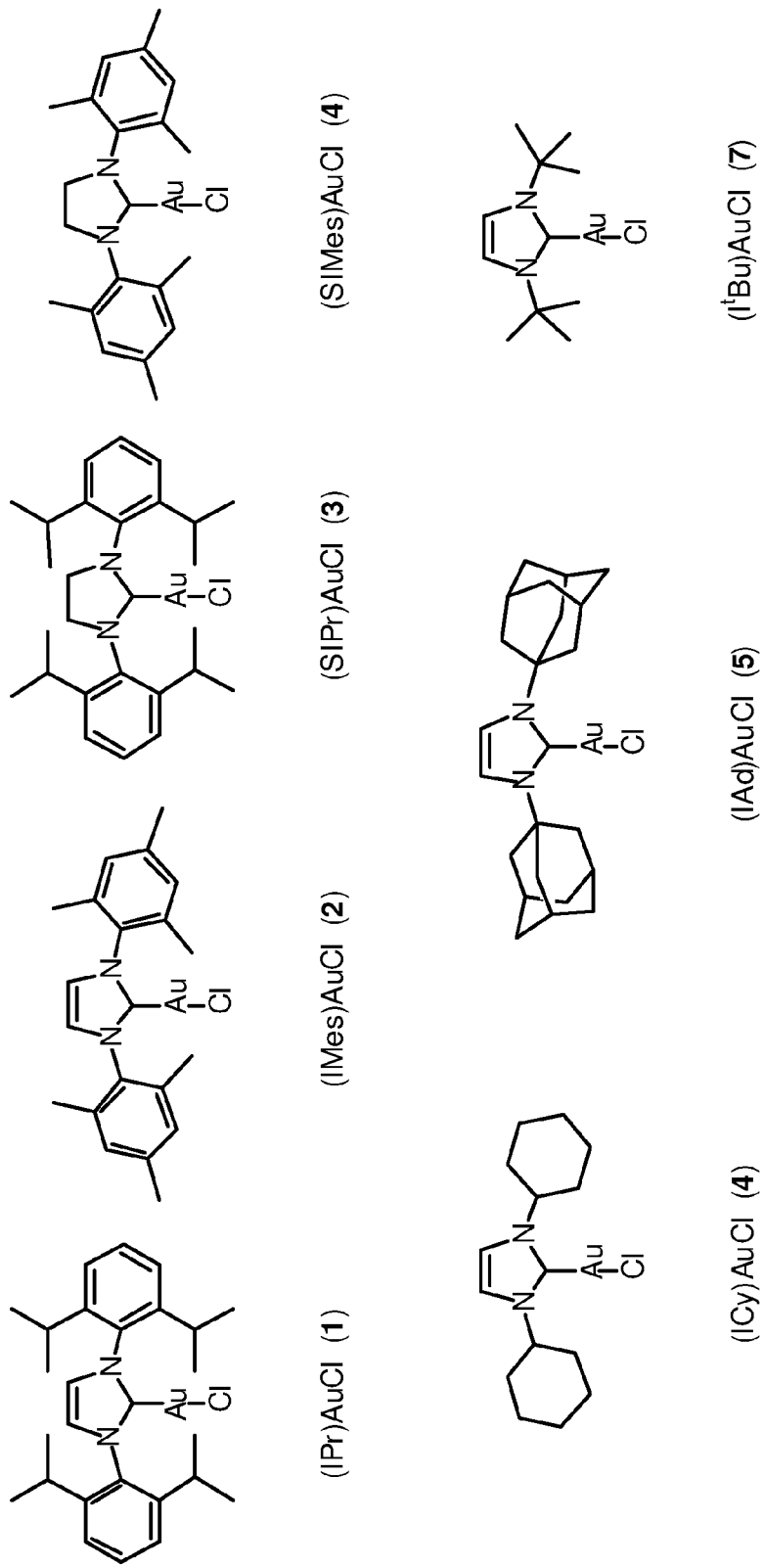
Figure 1: (NHC)Au(I)Cl complexes used as starting material in this study.

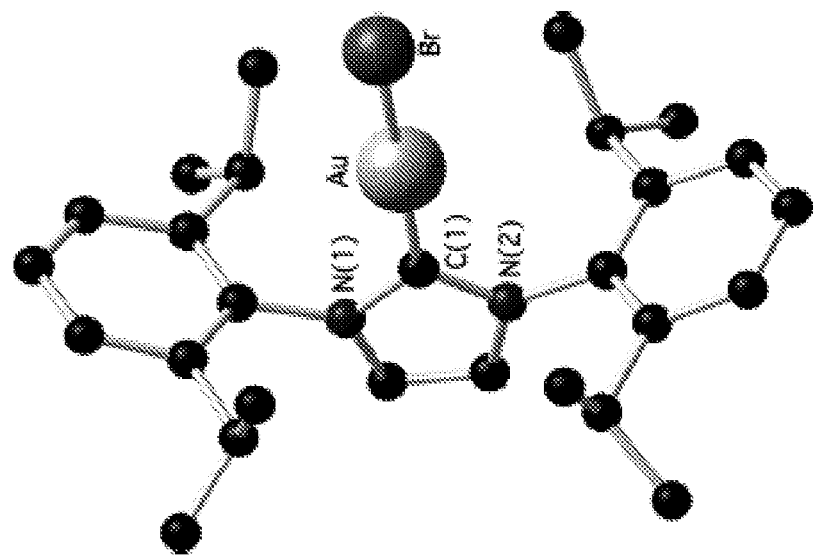
Figure 2: Ball and stick representation of (IPr)AuBr. Hydrogen atoms have been omitted for clarity.

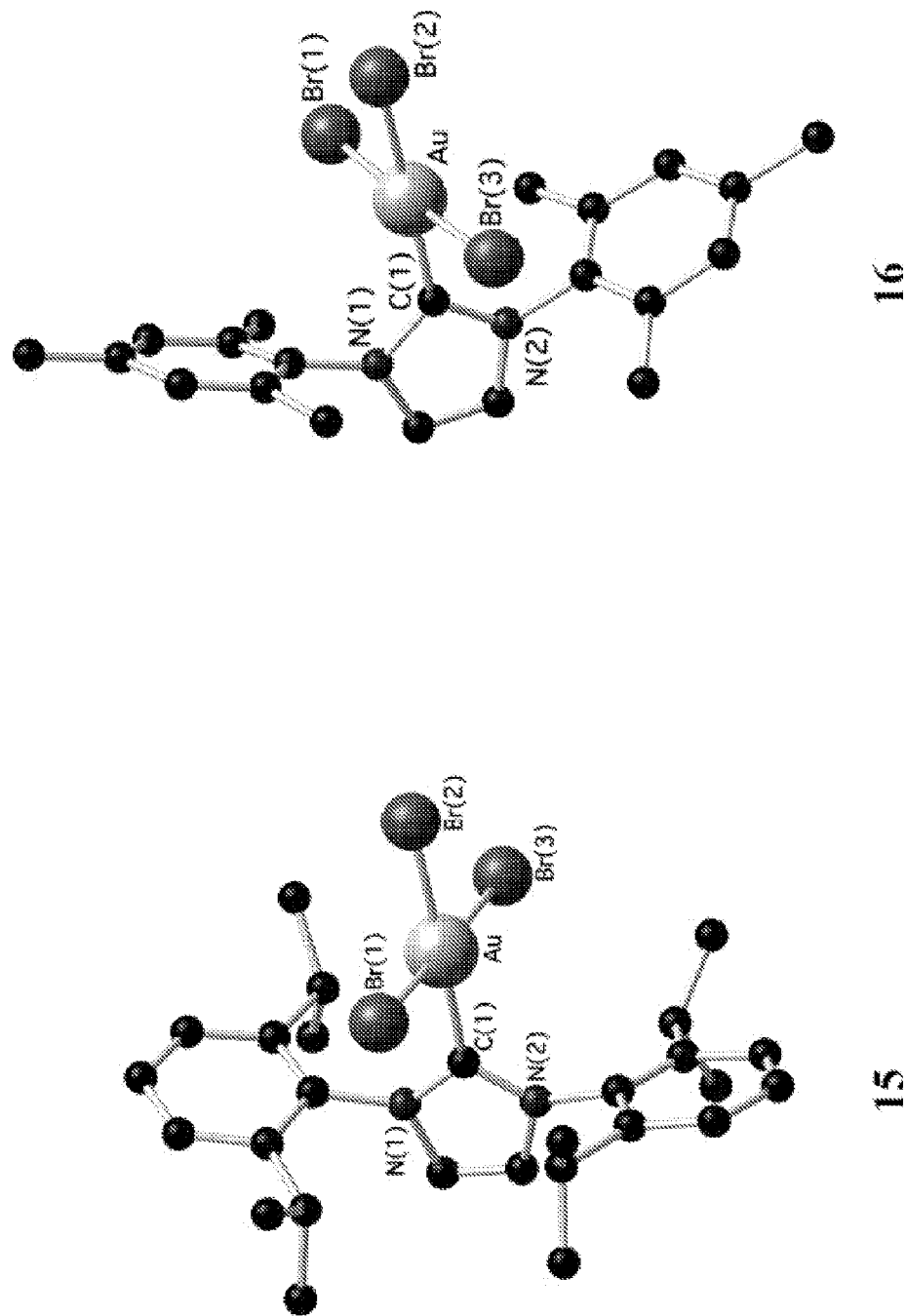
Figure 3: Ball and stick representation of (IPr)AuBr$_3$ (15) and (IMes)AuBr$_3$ (16). Hydrogen atoms have been omitted for clarity.

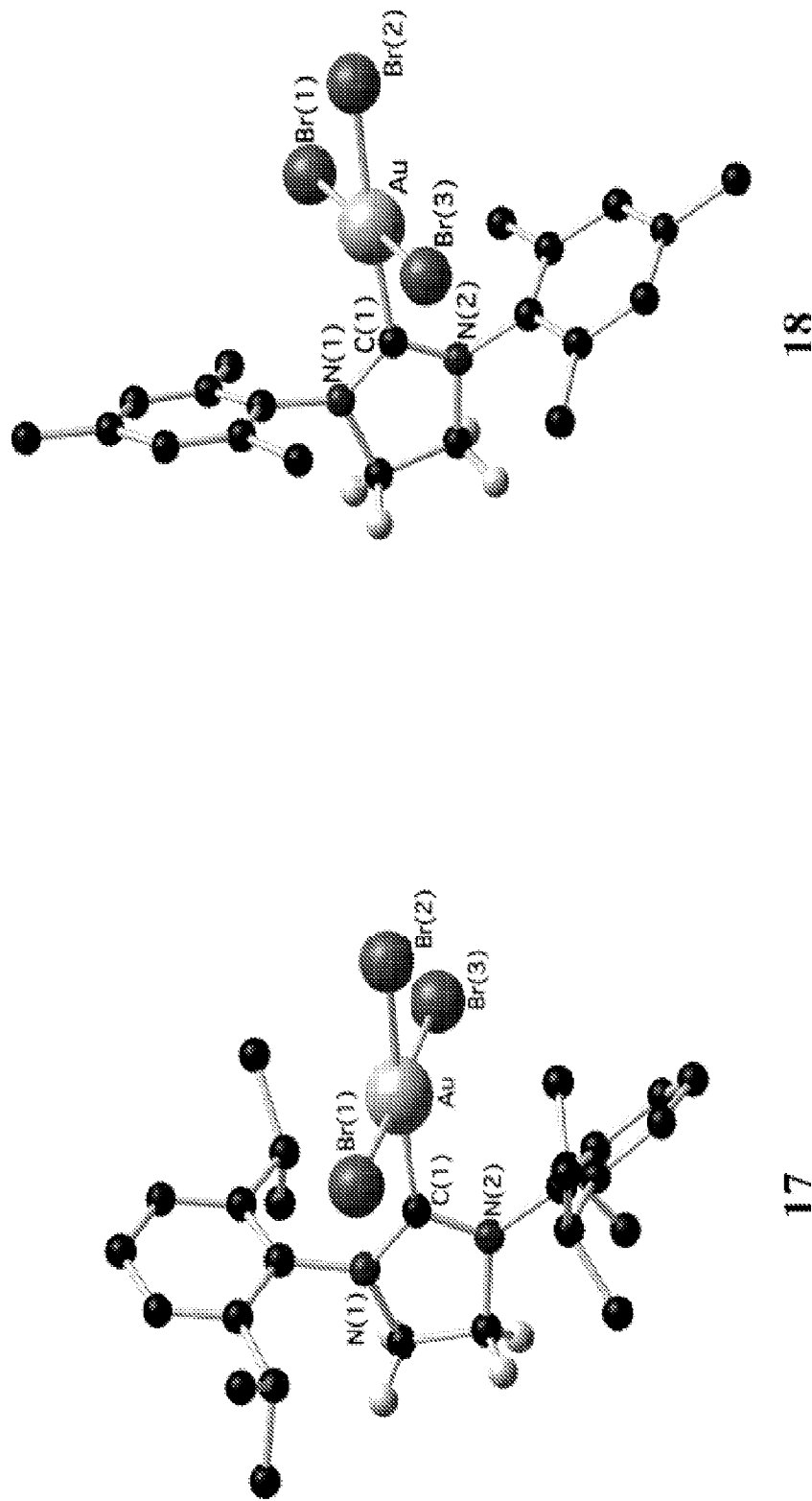
Figure 4: Ball and stick representation of (SIPr)AuBr₃ (17) and (SIMes)AuBr₃ (18). Most hydrogen atoms have been omitted for clarity.

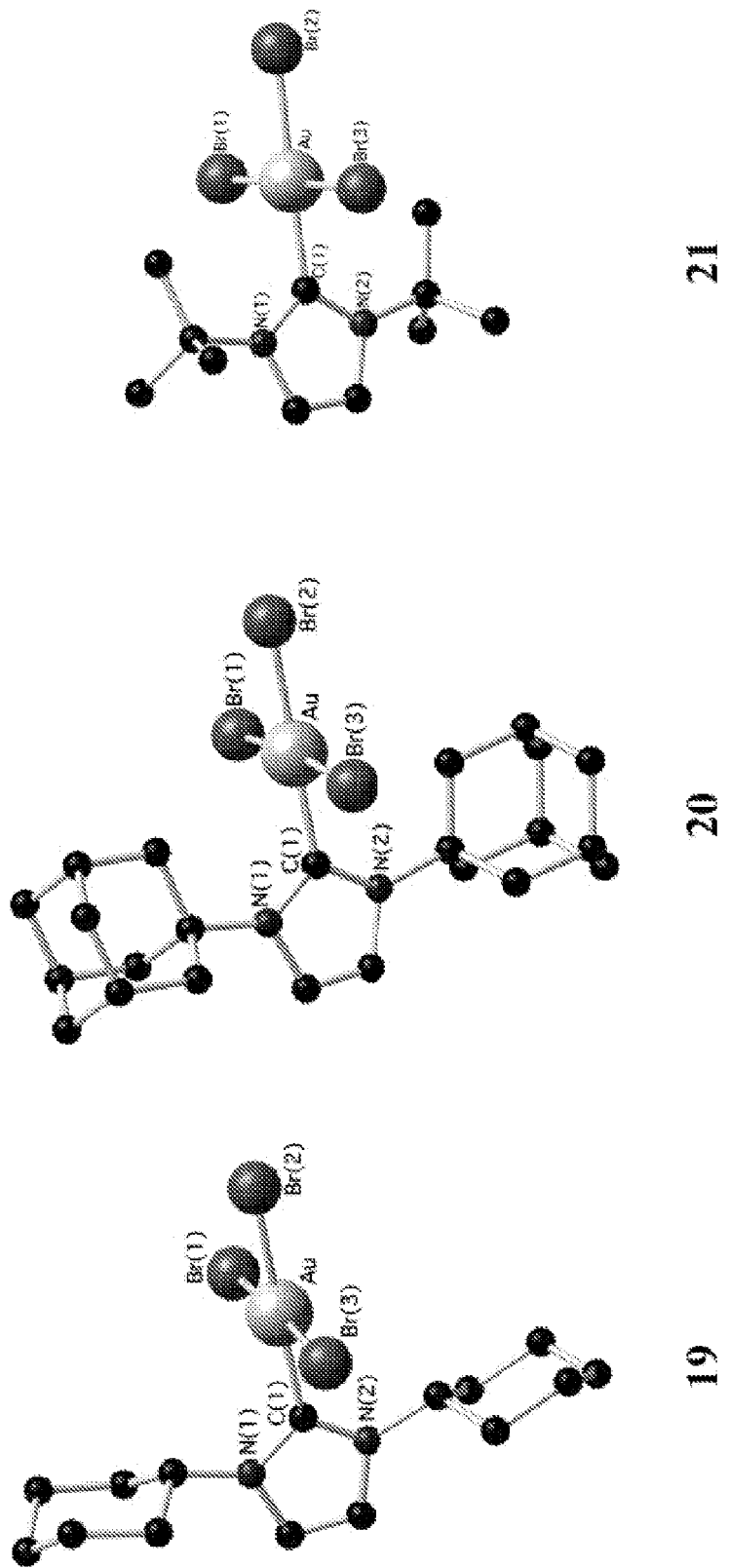
Figure 5: Ball and stick representation of (ICy)AuBr₃ (19) and (IAd)AuBr₃ (20) and (I$^t$Bu)AuBr₃ (21). Hydrogen atoms have been omitted for clarity.

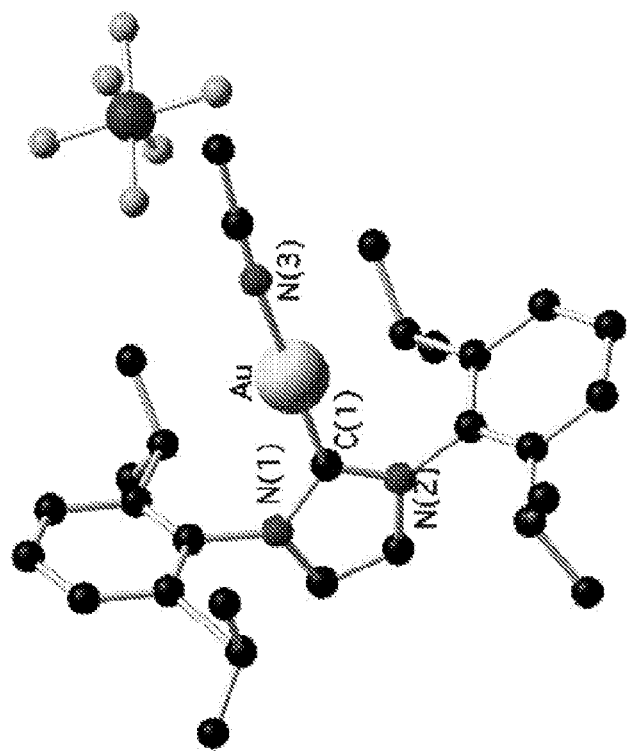
Figure 6: Ball-and-stick representations of [(IPr)Au$^+$(CH$_3$CN)][PF$_6$] (22) Hydrogens are omitted for clarity. Selected bond lengths and angle: C1–Au = 1.952(2) Å; N1–C1 = 1.38(2) Å; N2–C1 = 1.34(2) Å; Au–N3 = 2.022(2) Å; C1–Au–N3 = 177.9(8)°.

GOLD COMPLEXES FOR CATALYSIS AND PREPARATION THEREOF

CROSS-REFERENCE TO RELATED APPLICATIONS

Priority of our U.S. Provisional Patent Application Ser. No. 60/910,385, filed 5 Apr. 2007, incorporated herein by reference, is hereby claimed.

All of Steven P. NOLAN's prior U.S. and other patent applications and patents are incorporated herein by reference, including Ser. Nos. 09/392,869, 09/507,958, 09/907,526, 10/011,680 (application published as US2002/0173650), Ser. No. 10/092,753 (now U.S. Pat. No. 6,583,307), 10/653,688, 10/653,697, and 10/873,026.

This is not a continuation or continuation-in-part of any prior patent application.

STATEMENT REGARDING FEDERALLY SPONSORED RESEARCH OR DEVELOPMENT

This material is based upon work supported by the National Science Foundation (Contract No. CHE-0313852). Any opinions, findings, and conclusions or recommendations expressed in this material are those of the inventors and do not necessarily reflect the views of the National Science Foundation.

REFERENCE TO A "MICROFICHE APPENDIX"

Not applicable

BACKGROUND OF THE INVENTION

1. Field of the Invention

The present invention relates to gold(I) and gold(III) N-heterocyclic carbene (NHC) complexes. More particularly, the present invention relates to synthesis of cationic gold(I) N-heterocyclic carbene (NHC) complexes and neutral gold(III) N-heterocyclic carbene (NHC) complexes.

2. General Background of the Invention

Although, historically, organogold complexes have been underutilized in organic synthesis, numerous publications have recently emphasized the beneficial role of gold(I) in catalysis.[1] Organic transformations such as skeletal rearrangements (cycloisomerizations),[2] carbene transfer reactions,[3] indolizations,[4] oxidations,[5] and hydrosilylations,[6] are examples of the diverse chemistry mediated by organogold catalysts. Such transformations have been achieved with low catalyst loading and high turnover numbers. The gold(I) center must have two coordination sites occupied to ensure stability of the complexes and thereby avoid reduction to gold (0).[7] The most commonly employed ligands so far have been phosphines ($PR_3$),[8] and most recently N-heterocyclic carbenes (NHC).[9] Both ligand families exhibit strong σ-donation and coordination of such ligands result in good stability of the Au(I) complexes towards air, moisture and thermolysis. It is interesting to note that gold has even a stronger affinity for N-heterocyclic carbene than for phosphine and other Fisher acyclic carbenes.[10] A broad range of catalyzed transformations by inorganic gold(III) salts has been reported in the literature, examples include hydroaminations,[11] [4+2] benzannulations,[12] functionalization of aromatic C—H bonds,[13] cycloisomerizations,[14] and addition reactions to heterocycles.[15] Most often $AuX_3$ (X=Cl or Br) salts are directly used[11-16] and only a limited number of examples of well-defined organogold(III) complexes acting as catalysts are known.[17] No catalysis mediated by ($PR_3$)— or (NHC)Au(III) complexes has been reported so far. This is quite surprising since the chemistry of the arsine,[18] stilbine,[19] phosphine,[18b, 18c, 20] and carbene[21] gold(III) complexes, was first examined in the mid-1970's. Since these initial studies only a limited number of publications have focused on this chemistry. Notable exceptions are the extensive studies performed on gold(III) phosphine complexes by Schmidbaur et al.[22] Since then, C-tetrazolato,[23] bis-thiazolinylidene and bis-(NHC) gold(III) complexes bearing carbene moieties, have been published.[24] Nevertheless, no example of mono-(NHC) Au(III) complex has been reported, the mono-(4-methylthiazol-2-ylidene)$AuCl_3$ being the closest related complex reported so far.[24a]

For more information about the background of the present invention, see the papers entitled "Synthesis, isolation and characterization of cationic gold(I) N-heterocyclic carbene (NHC) complexes" *Chem. Commun.*, 2006, 2045-2047, and "Synthesis, Characterization and Reactivity of N-Heterocyclic Carbene Gold(III) Complexes." *Organometallics*, 2007, 26, 1376-1385, both attached to our U.S. Provisional Patent Application Ser. No. 60/910,385 and incorporated herein by reference.

BRIEF SUMMARY OF THE INVENTION

The present invention is an efficient route (which can be scaled up) to synthesize stable neutral and cationic gold complexes.

The cationic complexes are already activated and catalytically active. They don't require the use of a co-catalyst (generally made with silver salts). Also, they can be used as starting material to access gold complexes with uncommon ligands (such as a nitrogen and oxygen ligand, see e.g.: our publication with the auranofin mimic—S. Nolan et al., *Organometallics*, 2006, 25, 5824-5828, incorporated herein by reference.).

This is the first example of cationic (Mono-NHC) gold complexes using these (NHC)-ligands. These types of complexes were described as too unstable (reaction intermediate) to be isolated. This is the first example of (Mono-NHC) gold(III) complexes.

The present invention includes a stable complex of general formula $[(NHC)M-Ln]^{+p}Xm^{-q}$ where NHC is a carbene ligand; M is a metal; L is a two electron donor and X is a counteranion. Preferably, M=Au. Preferably, the carbene ligand is an N-heterocyclic carbene including imidazolyl-2-ylidene, imidazolidin-2-ylidene, tetrahydropyrimid-2-ylidene, thiazolium-based NHC, triazolium-based NHC. Preferably, L is acetonitrile, benzonitrile, THF, ether, pyridine, substituted pyridines, water, DMSO, DMF, DME, phosphines, phosphites, phosphinites, arsines, diene, Cl, Br and alkene. Preferably, n and m can be 0, 1, p and q can be 1, 3. Preferably, X is Cl, Br, I, BF4-, PF6-, SbF6-, AsF6-, B(C6H5) 4-, B(C6F5)4, NO3-, NO2-, ClO4-, ReO4, WO4-, MnO4-, SO42-, $PO_4$3-, and B(Ar)4 (in which case the Ar in B(Ar)4 is preferably substituted to various degrees with electron withdrawing group(s) preferentially, 2.5 CF3, NO2, sulfonates, Cl, Br, F, I, COOR).

Preferably, m=1.

The complex can advantageously be used in a cyclization reaction. The complex can advantageously be used in cyclization reactions involving an alkyne. The complex can advantageously be used in cyclization reactions involving an alkene. The complex can advantageously be used in cyclization reactions involving an amine. The complex can advantageously be used in cyclization reactions involving an alcohol.

The complex can advantageously be used in intermolecular coupling of alkyne and alkene. The complex can advantageously be used in intermolecular coupling of alkyne and amine. The complex can advantageously be used in intermolecular coupling of alkene and amine. The complex can advantageously be used in intermolecular coupling of alkyne and alcohol. The complex can advantageously be used in the formation of enones. The complex can advantageously be used in the formation of enals. The complex can advantageously be used in formation of esters. The complex can advantageously be used in hydrogenation of alkyne and alkene and other hydrogen transfers. The complex can advantageously be used for nucleophilic addition toward alkyne and alkene, such as addition of amines, heterocycles, carbanions, thiolates. The complex can advantageously be used for oxidation reactions.

A series of (NHC)Au(I) Cl [NHC=N,N'-bis(2,6-diisopropylphenyl)imidazol-2-ylidene or IPr (1), N,N'-bis(2,4,6-trimethylphenyl)imidazol-2-ylidene or IMes (2), N,N'-bis(2,6-diisopropylphenyl)imidazolin-2-ylidene or SIPr (3), N,N'-bis (2,4,6-trimethylphenyl)imidazolin-2-ylidene or SIMes (4), N,N'-bis(cyclohexyl)imidazol-2-ylidene or ICy (5), N,N'-bis (adamantyl)imidazol-2-ylidene or IAd (6), N,N'-bis(tert-Butyl)imidazol-2-ylidene or I$^t$Bu (7)] complexes were reacted with LiBr to generate [(IPr)AuBr] (8), [(IMes)AuBr] (9), [(SIPr)AuBr] (10), [(SIMes)AuBr] (11), [(ICy)AuBr] (12), [(IAd)AuBr] (13) and [(I$^t$Bu)AuBr] (14). These (NHC)Au(I) Br complexes underwent oxidative addition of elemental bromine leading to the new Au(III) complexes [(IPr)AuBr$_3$] (15), [(IMes)AuBr$_3$] (16), [(SIPr)AuBr$_3$] (17), [(SIMes)AuBr$_3$] (18), [(ICy)AuBr$_3$] (19), [(IAd)AuBr$_3$] (20), [(I$^t$Bu)AuBr$_3$] (21). Complete characterization by NMR spectroscopy and single crystal X-ray diffraction were performed in order to discern structural differences between organogold(I)/(III) congeners. A preliminary study examining the activity of (NHC)gold(III) species on the addition of water to alkynes is also presented.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein:

FIG. 1 shows (NHC)Au(I)Cl complexes used as starting material in this study.

FIG. 2 is a ball and stick representation of (IPr)AuBr in which hydrogen atoms have been omitted for clarity.

FIG. 3 is a ball and stick representation of (IPr)AuBr$_3$ (15) and (IMes)AuBr$_3$ (16) in which hydrogen atoms have been omitted for clarity.

FIG. 4 is a ball and stick representation of (SIPr)AuBr$_3$ (17) and (SIMes)AuBr$_3$ (18) in which most hydrogen atoms have been omitted for clarity.

FIG. 5 is a ball and stick representation of (ICy)AuBr$_3$ (19) and (IAd)AuBr$_3$ (20) and (I$^t$Bu)AuBr$_3$ (21) in which hydrogen atoms have been omitted for clarity.

FIG. 6 shows ball-and-stick representations of [(IPr)Au$^+$(CH$_3$CN)][PF$_6$$^-$](22) Hydrogens are omitted for clarity.

Selected bond lengths and angle: Cl—Au=1.952(2) Å; N1-Cl=1.38(2) Å; N2-Cl=1.34(2) Å; Au—N3=2.022(2) Å; Cl—Au—N3=177.9(8)°.

DETAILED DESCRIPTION OF THE INVENTION

Gold(III) N-Heterocyclic Carbene (NHC) Complexes

In order to expand the range of Au(III) complexes known and hopefully to provide access to novel Au(III) architectures, we reasoned that our prior expertise in NHC and Au(I) chemistry could be put to use in the synthesis of novel Au(III) complexes bearing the electron rich NHC ligands.

To eventually develop a general synthetic route leading to a family of (NHC)AuX$_3$ (X=halide) complexes, we initially examined possible approaches to a single target compound: (IPr)AuX$_3$. Previously, chlorine gas had been used to convert (thiazolinylidene)AuCl to (thiazolinylidene)AuCl$_3$.[24] Because of the very aggressive nature of chlorine gas, liquid bromine was selected as a halogenation agent as it does not require special safety equipment and allowed for a fairly straightforward and general synthetic protocol.

We first attempted to generate a NHC—Au(III) complex from a gold(III) salt, by direct reaction of the free carbene IPr (IPr=1,3-bis(2,6-diisopropylphenyl)imidazol-2-ylidene) with AuCl$_4$$^-$. The reaction led to the formation of yellow metallic gold(0). Study of the reaction mixture by $^1$H NMR spectroscopy, showed extensive sign of decomposition of the carbene and formation of (IPr)AuCl, in a low yield (20%). This result is not surprising as the gold(III) cation possesses a very strong oxidant character.[25] Indeed, reduction of tetrachloroauric acid (HAuCl$_4$) with a 2-fold excess of stibine, arsine, or phosphine ligands, is known to generate the corresponding gold(I) complexes in good yield.[25] (Scheme 1)

Scheme 1: Formation of gold(I) complexes by reduction of HAuCl$_4$.

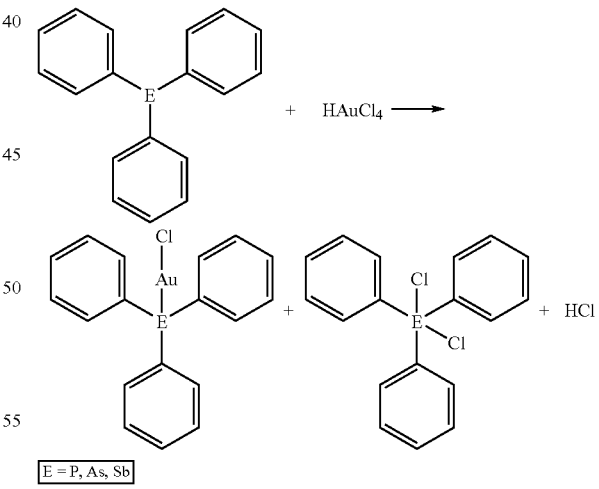

Oxidative addition of bromine by (IPr)AuCl (1) gave an orange powder in high yield. $^1$H NMR analysis provided a spectrum with the same pattern as the one found for (IPr) AuCl, but with significant change in the chemical shifts for all protons. We also noticed that the septuplet assigned to the protons from the diisopropyl group, was split into two distinct multiplets at 2.99 and 2.96 ppm. We attribute this small splitting to the existence of two different complexes: (IPr)AuBr$_3$ and (IPr)AuBr₂Cl. ¹³C NMR spectra also support this hypothesis as two complexes with a similar carbon skeleton and very close signals are observed.

To exclude the formation of a mixture of (IPr)AuBr$_{3-x}$Cl$_x$, we proceeded to convert the reported[7a,26] (NHC)Au(I) chloride complexes (1-7): (1,3-bis(2,6-diisopropylphenyl)imidazol-2-ylidene) gold(I) chloride (IPr)AuCl[26] (1), (1,3-bis(2,4,6-trimethylphenyl)imidazol-2-ylidene) gold(I) chloride (IMes)AuCl[26] (2), (1,3-bis(2,6-diisopropylphenyl)imidazolidin-2-ylidene) gold(I) chloride (SIPr)AuCl[26] (3), (1,3-bis(2,4,6-trimethylphenyl)imidazolidin-2-ylidene) gold(I) chloride (SIMes)AuCl[26] (4), (1,3-bis(cyclohexyl)imidazol-2-ylidene) gold(I) chloride (ICy)AuCl[26] (5), (1,3-bis(adamantyl)imidazol-2-ylidene) gold(I) chloride (IAd) AuCl[26] (6), (1,3-bis(tert-butyl)imidazol-2-ylidene) (I$^t$Bu)AuCl[7a] (7) (FIG. 1) into their (NHC)Au(I) bromide relatives (8-14) by use of a metathetical reaction with LiBr. The gold(I) cation being one of the softest available acids, we suspected the bromide anion would easily replace the chloride anion.

The complexes (NHC)AuCl (1-7) were stirred with a large excess of lithium bromide, at room temperature, with acetone or THF as solvent. The reactions are not sensitive to air and provide the desired bromide complexes (IPr)AuBr (8), (IMes)AuBr (9), (SIPr)AuBr (10), (SIMes)AuBr (11), (ICy) AuBr (12), (IAd)AuBr (13) and (I$^t$Bu)AuBr (14) as white powders (Equation 1). The protocol furnishes the products in good yields after stirring for 24 hours.

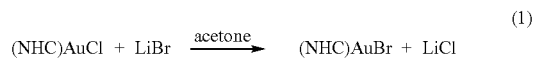

(1)

It is interesting to note that while these complexes are air-stable, the presence of water leads to rapid decomposition with appearance of purple colloidal gold(0) and formation of imidazolium salts. This trend is strongly accentuated for complexes bearing saturated carbene moieties (10 and 11). While Baker et al.[7a] reported a reaction time of 16 hours to convert (I$^t$Bu)AuCl (7) into (I$^t$Bu)AuBr (14), we selected a longer reaction time of 24 hours as a general reaction time as we noticed that the metathesis reaction could require longer time to reach completion as a function of the NHC. This reaction time is then general and not optimized for each NHC employed. The ¹H NMR spectra of complexes 8, 9, 12, 13 and 14 display a low field singlet between 6.95 and 7.17 ppm assigned to the two protons located on the unsaturated imidazole backbone. Spectra of complexes 10 and 11 display a more upfield singlet at 4.04 and 3.97 ppm respectively, assigned to the four protons located on the saturated imidazole backbone. For all complexes, all signals expected for the N-aryl, and N-alkyl chains are present. As expected, no significant change in the chemical shift (less than 0.1 ppm) is visible for the signals attributed to congeners of the (NHC) AuCl and (NHC)AuBr series. The substitution of a chloride by a bromide has a very small effect on the environment seen by the protons of the different complexes. ¹³C NMR spectra display resonances for the different carbenic carbons between 166.3 and 175.1 ppm for the unsaturated imidazole moieties and around 195 ppm for the saturated imidazole moieties. (Table 1) The intensity of this resonance is weak since the carbenic carbon is a quaternary center and is affected by the quadrupolar moment of the gold atom (I=3/2).

TABLE 1

Chemical shifts of the carbenic carbon in NMR for the gold(I) halides complexes.

| (NHC)AuCl | $\delta_C$ (ppm) | (NHC)AuBr | $\delta_C$ (ppm) | $\Delta \delta_C$ (ppm) |
|---|---|---|---|---|
| (IPr)AuCl$^a$ (1) | 175.1 | (IPr)AuBr$^b$ (8) | 179.0 | +3.9 |
| (IMes)AuCl$^b$ (2) | 173.4 | (IMes)AuBr$^b$ (9) | 176.7 | +3.3 |
| (SIPr)AuCl$^b$ (3) | 196.1 | (SIPr)AuBr$^b$ (10) | 199.0 | +2.9 |
| (SIMes)AuCl$^b$ (4) | 195.0 | (SIMes)AuBr$^b$ (11) | 198.1 | +3.1 |
| (ICy)AuCl$^a$ (5) | 168.0 | (ICy)AuBr$^b$ (12) | 172.1 | +4.1 |
| (IAd)AuCl$^a$ (6) | 166.3 | (IAd)AuBr$^b$ (13) | 170.2 | +3.9 |
| (I$^t$Bu)AuCl$^a$ (7) | 168.2 | (I$^t$Bu)AuBr$^b$ (14) | 172.4 | +4.2 |

$^a$NMR recorded in CD$_2$Cl$_2$.
$^b$NMR recorded in CDCl$_3$.

Herrmann et al.[27] have postulated that the chemical shift of the carbenic carbon can be correlated to the acidity of the metal to which the NHC is bound. Indeed a free NHC ligand, with no electronic donation toward a Lewis acid would have a very low-field signal, usually above 200 ppm, reflecting the availability of an excess of electron density on the carbene carbon. In contrast, a bond with a metal will displace the chemical shift to a higher field value when the electronic density from the carbene is partially transferred to the metal by sigma donation. By comparing the chemical shifts of the carbenic carbon, between the chloride and the bromide series of the gold(I) complexes, a consistent shift of 3 to 4 ppm to lower field due the halide exchange was observed that we attribute to a small variation of the acidity of the gold center. We reasoned that the metal acidity is less due to the lower electronegativity of bromine versus chlorine. This result is in good agreement with the study published by Baker et al.[7a] Crystals of (IPr)AuBr (8) were grown by slow diffusion in a mixture of DCM/hexane and allowed us to perform a single crystal X-ray diffraction study. (FIG. 2)

The gold atom is two coordinate, as usual for gold(I) complexes, and exhibits a linear geometry with a C(1)-Au—Br bond angle value of 180.0°. The C(1)-Au bond length (1.975 Å) is in good agreement with reported NHC gold(I) complexes.[7a, 26, 28] The Au—Br bond length (2.381 Å) is in the range of known bromide gold(I) salts and complexes.[7a, 29] The minimal Au . . . Au distance is 8.431 Å, excluding any aurophilic interactions, which require a distance shorter than 3.60 Å between gold(I) cations.[30] There is no major structural difference between the (IPr)AuCl (1) and (IPr)AuBr (8). Crystals of other (NHC)AuBr complexes, described in this paper, can be grown in a mixture of DCM/heptane.

Direct addition of a slight excess of elemental bromine (Br$_2$) to a solution of (IPr)AuBr (8), (IMes)AuBr (9), (SIPr) AuBr (10), (SIMes)AuBr (11), (ICy)AuBr (12), (IAd)AuBr (13) and (I$^t$Bu)AuBr (14) complexes, gives the desired (IPr) AuBr$_3$ (15), (IMes)AuBr$_3$ (16), (SIPr)AuBr$_3$ (17), (SIMes) AuBr$_3$ (18), (ICy)AuBr$_3$ (19), (IAd)AuBr$_3$ (20) and (I$^t$Bu) AuBr$_3$ (21) complexes in good yields, as yellow or orange powders stable in air. (Equation 2)

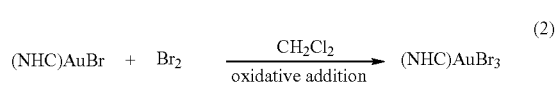

(2)

Initially, the reactions were allowed to proceed overnight but we noticed that the reactions were very fast at room temperature (even at −78° C.), and completed in less than half hour. This is not surprising since redox reactions involving metals, are known to proceed with a rapid kinetic. We did not observe any NHC—Au bond cleavage or rearrangement by using bulky carbenes, such as IAd and I'Bu, as reported for the oxidation of sterically demanding gold(I) phosphines.[22b] Attempts to synthesize (IMes)AuBr$_3$ (16) and (SIMes)AuBr$_3$ (18) at room temperature failed and gave decomposition product with no trace of the desired complexes, even when a sub-stoichiometric amount of bromine was used. At —78° C., the reaction proceeded smoothly without any trace of decomposition product. These particular synthetic conditions for the complexes bearing the IMes and SIMes moieties, again illustrate the difference in reactivity encountered with these two carbenes on the chemistry of metals from group 11.[26, 28c, 31] (Scheme 2)

Scheme 2: Reactivity of complexes bearing diffrent NHC moieties.

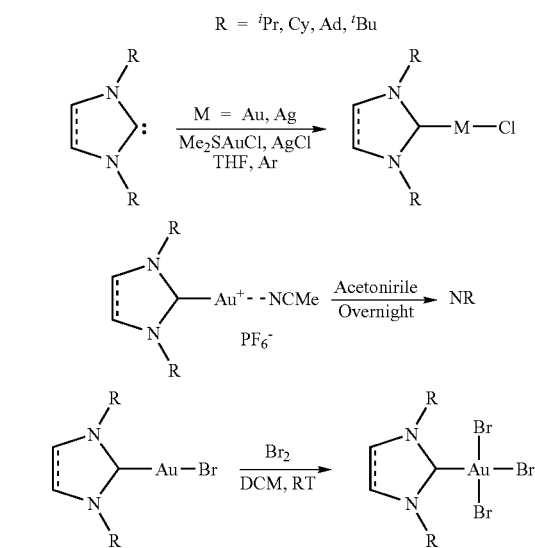

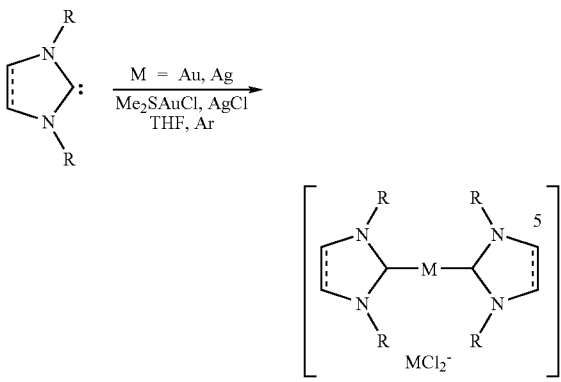

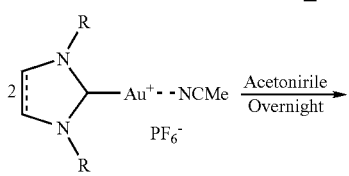

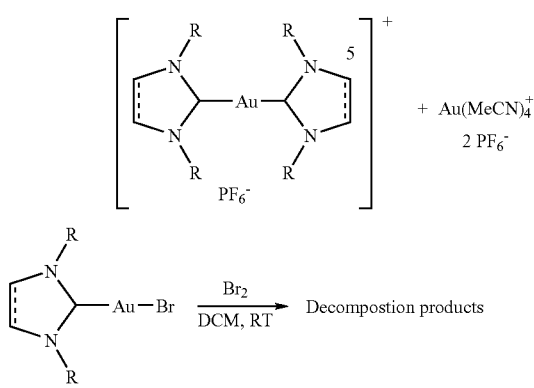

The $^1$H NMR spectra of the complexes 15, 16, 19, 20, and 21 display a low field singlet between 7.21 and 7.53 ppm assigned to the two protons located on the unsaturated imidazole backbone. The chemical shifts are slightly shifted down-field, when compared to the (NHC)AuBr series, likely due to a double bond being less rich in electron density. It is reasonable to assume that gold(III) being more acidic than gold(I) induces a greater delocalization of the electronic density from the carbon-carbon double bond to the carbenic carbene, through the entire aromatic system. There is no sign of attack by the bromine on the double bond. $^1$H NMR Spectra of 17 and 18 display a more up field singlet at 4.29 and 4.23 ppm respectively, assigned to the four protons located on the saturated imidazole backbone. For all complexes, signals expected for the N-aryl, and N-alkyl chains are present. $^{13}$C NMR resonances of the different carbenic carbons are characterized by a weak upfield signal between 132.9 and 146.2 ppm for the unsaturated imidazole moieties and around 173 ppm for the saturated imidazole moieties. (Table 2)

TABLE 2

NMR Chemical shifts of the carbenic carbon for the Au—Br complexes.

| (NHC)AuBr | $\delta_C$ (ppm) | (NHC)AuBr$_3$ | $\delta_C$ (ppm) | $\Delta\delta_C$ (ppm) |
|---|---|---|---|---|
| (IPr)AuBr$^a$ (8) | 179.0 | (IPr)AuBr$_3$$^a$ (15) | 146.2 | −32.8 |
| (IMes)AuBr$^a$ (9) | 176.7 | (IMes)AuBr$_3$$^a$ (16) | 144.4 | −32.3 |
| (SIPr)AuBr$^a$ (10) | 199.0 | (SIPr)AuBr$_3$$^a$ (17) | 174.1 | −24.9 |
| (SIMes)AuBr$^a$ (11) | 198.1 | (SIMes)AuBr$_3$$^a$ (18) | 172.3 | −25.8 |
| (ICy)AuBr$^a$ (12) | 172.1 | (ICy)AuBr$_3$$^a$ (19) | 136.8 | −35.3 |
| (IAd)AuBr$^a$ (13) | 170.2 | (IAd)AuBr$_3$$^a$ (20) | 132.9 | −37.3 |
| (I'Bu)AuBr$^a$ (14) | 172.4 | (I'Bu)AuBr$_3$$^a$ (21) | 134.2 | −38.3 |

| (NHC)•HCl | $\delta_C$ (ppm) | $\Delta\delta_C$ (ppm) |
|---|---|---|
| (IPr)•HCl$^b$ | 132.2 | +14.0 |
| (IMes)•HCl$^b$ | 134.8 | +9.6 |
| (SIPr)•HCl$^b$ | 160.0 | +14.1 |
| (SIMes)•HCl$^b$ | 160.2 | +12.1 |
| (ICy)•HCl$^b$ | 134.5 | +2.3 |

TABLE 2-continued

| | | |
|---|---|---|
| (IAd)•HCl[b] | 132.1 | +0.8 |
| (I$^t$Bu)•HCl[b] | 132.7 | +1.5 |

[a]NMR recorded in CDCl$_3$.
[b]NMR recorded in DMSO-d$_6$.

The differences of the carbenic carbon shifts between the two series of gold bromide complexes are found between 24.9 and 38.3 ppm. However, it is within the range reported for the oxidation of chloride gold(I) thiazolinylidene by Raubenheimer et al.[24] Expectedly, it indicates an increase of acidity of the gold atom associated with an increase in oxidation state. (Table 2) It is reasonable to assume that a smaller upfield shift indicates an attenuated acidity of the gold atom, likely due to a better donation of the carbene moieties. If this is correct, the saturated SIPr and SIMes carbenes provide the greatest electronic density to the gold(III) cation. A comparison between unsaturated carbenes bearing aromatic and alkyl R-groups, is also possible. Interestingly, IPr and IMes appear to be better σ-donors than IAd, ICy and I$^t$Bu. All NHC-ligands display the same donor property trend as seen for the gold(I) complexes.[26] It is also interesting to note that the chemical shifts of the carbenic carbon in these gold(III) complexes, especially the alkyl R-group bearing complexes, are extremely close to the reported value for the imidazolium salts, with a difference of 0.9 to 2.3 ppm. Unfortunately, we cannot unequivocally quantify in an absolute sense the electronic effect associated with electronic density residing on the carbenic carbene as the —Au(III)Br$_3$ moiety is not isolobal with the acidic proton born by imidazolium salts.[7a]

To unambiguously characterize all these new gold(III) complexes, X-ray quality crystals were grown in a mixture of DCM/heptane. Ball and stick representations are provided in FIGS. 3, 4 and 5.

All (NHC)AuBr$_3$ complexes have a four-coordinate gold atom, in a square planar environment, as expected for d$^8$ metals. The C(1)-Au—Br(2) and Br(1)-Au—Br(3) bonds are nearly linear with angles between 173.73° and 178.66° (Table 3).

All C(1)-Au distances lie in the range of 2.01 and 2.05 Å, whether the gold center bears a saturated or unsaturated imidazol motif. (Table 4) These metrical parameters are in close agreement with reported organogold(III) complexes[20c, 32] possessing carbon-gold bond lengths between 2.01 and 2.07 Å. There is no discernable correlation between the gold-carbon bond length and the electronic or steric parameters associated with the NHCs employed.

TABLE 4

Selected Au—X bond distanced (Å) in (NHC)AuBr$_3$ complexes.

| (NHC)AuBr$_3$ | Au—C(1) | Au—Br(1) | Au—Br(2) | Au—Br(3) |
|---|---|---|---|---|
| (IPr)AuBr$_3$ (15) | 2.048(19) | 2.384(3) | 2.386(4) | 2.397(3) |
| (IMes)AuBr$_3$ (16) | 2.009(8) | 2.4156(15) | 2.4224(12) | 2.4123(14) |
| (SIPr)AuBr$_3$ (17) | 2.042(13) | 2.405(2) | 2.4452(18) | 2.408(2) |
| (SIMes)AuBr$_3$ (18) | 2.052(13) | 2.4108(15) | 2.4468(17) | 2.4169(17) |
| (ICy)AuBr$_3$ (19) | 2.04(2) | 2.405(3) | 2.444(3) | 2.410(3) |
| (IAd)AuBr$_3$ (20) | 2.052(6) | 2.4465(8) | 2.4496(7) | 2.4426(7) |
| (I$^t$Bu)AuBr$_3$ (21) | 2.015(5) | 2.4209(6) | 2.4403(6) | 2.4638(6) |

All Br—Au distances were found to be between 2.38 and 2.47 Å. (Table 4) They are similar to reported Br—Au(III) complexes where the bromide-gold(III) bond lengths are between 2.38 and 2.65 Å.[22b,33] The carbene ligands (except IPr and IAd) induce a trans-influence with a lengthening of the Au—Br(2) bond. This effect is less pronounced than the one observed for the phosphine-AuBr$_3$ complexes described by Schmidbaur et al.[22b] It is surprising to observe that while there is no visible trans-effect for the complex (IAd)AuBr$_3$ (20), the three different Au—Br bonds are slightly longer than expected when compared to our other gold(III) complexes. There is no close contact between gold atoms. This is not surprising since aurophilic interactions only apply for d$^{10}$ gold(I) cations.[34] There is no insertion of bromine in the crystals lattices, as reported for some phosphine gold(III) tribromide complexes.[22b]

TABLE 3

Selected bond angles values (deg) for (NHC)AuBr$_3$ complexes.

| (NHC)AuBr$_3$ | C(1)—Au—Br(1) | C(1)—Au—Br(2) | C(1)—Au—Br(3) |
|---|---|---|---|
| (IPr)AuBr$_3$ (15) | 92.3(5) | 178.2(5) | 88.8(5) |
| (IMes)AuBr$_3$ (16) | 91.4(2) | 178.0(2) | 89.1(2) |
| (SIPr)AuBr$_3$ (17) | 88.0(4) | 174.9(4) | 93.0(4) |
| (SIMes)AuBr$_3$ (18) | 91.0(4) | 175.9(4) | 90.9(4) |
| (ICy)AuBr$_3$ (19) | 89.2(6) | 178.3(6) | 86.4(6) |
| (IAd)AuBr$_3$ (20) | 87.80(15) | 178.66(16) | 85.93(15) |
| (I$^t$Bu)AuBr$_3$ (21) | 90.69(14) | 177.97(14) | 87.16(14) |

| (NHC)AuBr$_3$ | Br(1)—Au—Br(2) | Br(1)—Au—Br(3) | Br(2)—Au—Br(3) |
|---|---|---|---|
| (IPr)AuBr$_3$ (15) | 87.66(15) | 178.79(12) | 91.21(16) |
| (IMes)AuBr$_3$ (16) | 89.69(7) | 177.78(5) | 89.83(6) |
| (SIPr)AuBr$_3$ (17) | 89.89(7) | 177.76(4) | 89.28(7) |
| (SIMes)AuBr$_3$ (18) | 88.71(7) | 176.60(7) | 89.66(7) |
| (ICy)AuBr$_3$ (19) | 91.92(11) | 175.45(11) | 92.51(10) |
| (IAd)AuBr$_3$ (20) | 93.53(2) | 173.73(3) | 92.73(2) |
| (I$^t$Bu)AuBr$_3$ (21) | 91.32(2) | 177.82(2) | 90.83(3) |

TABLE 5

Crystallographic data for complexes 8 and 15-21.

| | Complex | | | |
|---|---|---|---|---|
| | 8 | 15 | 16 | 17 |
| Formula | $C_{27}H_{36}N_2AuBr$ | $C_{27.50}H_{37}N_2AuBr_3$ | $C_{21}H_{24}N_2AuBr_3$ | $C_{28}H_{40}N_2AuBr_3Cl_2$ |
| $M_r$ | 665.45 | 867.74 | 741.12 | 912.22 |
| Crystal system | orthorhombic | monoclinic | orthorhombic | monoclinic |
| Space group | Pccn | P2(1)/n | P2(1)2(1)2(1) | P2(1)/c |
| Cells constants | | | | |
| a (Å) | 10.9117(6) | 16.950(2) | 10.6845(6) | 10.677(2) |
| b (Å) | 12.6771(7) | 19.403(3) | 14.2833(8) | 16.593(4) |
| c (Å) | 19.9643(10) | 20.417(3) | 15.7115(9) | 19.306(4) |
| α(deg) | 90.00 | 90.00 | 90.00 | 90.00 |
| β(deg) | 90.00 | 110.421(3) | 90.00 | 99.664(4) |
| γ(deg) | 90.00 | 90.00 | 90.00 | 90.00 |
| V (Å$^3$) | 2761.6 (3) | 6293.0(15) | 2397.7(2) | 3371.5(12) |
| Z | 4 | 8 | 4 | 4 |
| λ (Å) | 0.71073 | 0.71073 | 0.71073 | 0.71073 |
| ρ (calcd) (g/cm$^3$) | 1.601 | 1.832 | 2.053 | 1.797 |
| μ, mm$^{-1}$ | 6.789 | 8.588 | 11.143 | 8.096 |
| F(000) | 1304 | 3336 | 1392 | 1760 |
| T (K) | 295(2) | 295(2) | 295(2) | 295(2) |
| 2θ$_{max}$ (deg) | 55.04 | 52.774 | 46.718 | 53.004 |
| No. of rflns measd | 17717 | 39800 | 25184 | 16323 |
| No. of indep rflns | 3140 | 8206 | 3137 | 4009 |
| R$_{int}$ | 0.0505 | 0.0574 | 0.0410 | 0.0820 |
| No. of data/restraints/params | 2026/0/146 | 5509/563/638 | 2891/705/330 | 2934/335/377 |
| R$_w$ (F$^2$ all rflns) | 0.0758 | 0.0967 | 0.0701 | 0.0992 |
| R(F, >4σ(F)) | 0.0321 | 0.0495 | 0.0300 | 0.0589 |
| Max Δρ (e Å$^{-3}$) | 0.928 and −0.986 | 0.925 and −1.413 | 0.744 and −0.530 | 1.130 and −0.775 |

| | Complex | | | |
|---|---|---|---|---|
| | 18 | 19 | 20 | 21 |
| Formula | $C_{21.50}H_{27.01}N_2AuBr_3Cl_{1.01}$ | $C_{15.50}H_{25}N_2AuBr_3Cl$ | $C_{23}H_{32}N_2AuBr_3$ | $C_{11}H_{20}N_2AuBr_3$ |
| $M_r$ | 785.90 | 711.52 | 773.20 | 616.99 |
| Crystal system | monoclinic | orthorhombic | monoclinic | monoclinic |
| Space group | P2(1)/c | Pccn | P2(1)/c | P2(1)/c |
| Cells constants | | | | |
| a (Å) | 8.7226(8) | 15.0878(9) | 16.4445(16) | 9.2947(5) |
| b (Å) | 16.0470(15) | 19.9495(13) | 11.1131(10) | 15.3944(8) |
| c (Å) | 19.7576(18) | 14.6881(9) | 12.9782(12) | 12.1528(7) |
| α(deg) | 90.00 | 90.00 | 90.00 | 90.00 |
| β(deg) | 95.611(2) | 90.00 | 90.044(2) | 96.7460(10) |
| γ(deg) | 90.00 | 90.00 | 90.00 | 90.00 |
| V (Å$^3$) | 2752.3(4) | 4421.0(5) | 2371.8(4) | 1726.86(16) |
| Z | 4 | 8 | 4 | 4 |
| λ (Å) | 0.71073 | 0.71073 | 0.71073 | 0.71073 |
| ρ (calcd) (g/cm$^3$) | 1.897 | 2.138 | 2.165 | 2.373 |
| μ, mm$^{-1}$ | 9.808 | 12.198 | 11.270 | 15.445 |
| F(000) | 1485 | 2664 | 1472 | 1136 |
| T (K) | 295(2) | 295(2) | 295(2) | 295(2) |
| 2θ$_{max}$ (deg) | 61.21 | 58.484 | 46.718 | 52.846 |
| No. of rflns measd | 39906 | 36155 | 21229 | 21428 |
| No. of indep rflns | 3600 | 2892 | 3429 | 3569 |
| R$_{int}$ | 0.0603 | 0.0586 | 0.0494 | 0.0418 |
| No. of data/restraints/params | 3197/240/278 | 2609/186/217 | 2888/280/390 | 3107/491/235 |
| R$_w$ (F$^2$ all rflns) | 0.1291 | 0.1339 | 0.0725 | 0.0548 |
| R(F, >4σ(F)) | 0.0490 | 0.0438 | 0.0295 | 0.0259 |
| Max Δρ (e Å$^{-3}$) | 1.610 and −0.797 | 0.778 and −1.198 | 1.244 and −1.443 | 1.127 and −0.907 |

We were interested to test the catalytic activity of our new well-defined gold(III) complexes to mediate the addition of water to alkynes. As gold(I) and gold(III) salts are known to catalyze this reaction, we used the reported work[1a, 17a, 35] as references to gauge the catalytic activity of our system. Of the many Au(III) complexes synthesized, (IPr)AuBr$_3$ displays the best catalytic activity. (Table 6)

The solvent screening indicates that an alcohol is required for the catalysis to proceed efficiently. (Table 7) There is no trace of enol ethers or acetals resulting from the addition of alcohol to the alkynes as a competing reaction.

TABLE 6

Screening of (NHC)AuBr3 complexes in addition of water to alkynes.

| entry | catalyst | time | yield[b] |
|---|---|---|---|
| 1 | — | — | NR |
| 2 | IPr | — | NR |
| 3 | AuCl$_3$ | 24 h | 94% |
| 4 | (IPr)AuBr$_3$ | 24 h | 95% |
| 5 | (IMes)AuBr$_3$ | 24 h | 91% |
| 6 | (IAd)AuBr$_3$ | 48 h | 35% |
| 7 | (ItBu)AuBr$_3$ | 48 h | 92% |

[a]Reaction conditions: 10 mol % of catalyst, 0.5 mL of H$_2$O, 0.5 mL of methanol, 1 mmol of phenylacetylene.
[b]GC yields, an average of two runs.

TABLE 7

Solvent screening in addition of water to alkynes.

| entry | solvent | time | yield[b] |
|---|---|---|---|
| 1 | MeGH | 24 h | 95% |
| 2 | IPA | 36 h | 47% |
| 3 | H$_2$O | 48 h | 62%[c] |
| 4 | MeCN | — | NR |
| 5 | THF | — | NR |

[a]Reaction conditions: 10 mol % of catalyst, 0.5 mL of H$_2$O, 0.5 mL of methanol, 1 mmol of phenylacetylene.
[b]GC yields, an average of two runs.
[c]Small amount of acetone added to solubilize the catalyst.

The present complexes were inefficient with internal alkynes, confirming the likely formation of a gold(III) vinyl secondary carbocation as an early reaction intermediate[14d, 35] (Table 8).

TABLE 8

Various alkynes screened in addition of water to alkynes.

| entry | alkyne | cat. loading | time | yield (%)[b] |
|---|---|---|---|---|
| 1 | Me$_2$N-C$_6$H$_4$-C≡CH | 10 mol% | 1 h | 100 (92)[c] |
| 2 | MeO-C$_6$H$_4$-C≡CH | 10 mol % | 6 h | 96 (90) |
| 3 | PhC≡CH | 10 mol % | 24 h | 95 (88) |
| 4 | NC-CH$_2$-C$_6$H$_4$-C≡CH | 10 mol % | 36 h | 92 (86) |
| 5 | Ph$_2$C(OH)C≡CH | 10 mol % | 3 h | 40 (36) |

TABLE 8-continued

Various alkynes screened in addition of water to alkynes.

| entry | alkyne | cat. loading | time | yield (%)[b] |
|---|---|---|---|---|
| 6 | Cl-C6H4-C≡CH | 10 mol % | 36 h | 80 (77) |
| 7 | hex-2-yne (alkyl internal alkyne) | 10 mol % | — | NR |
| 8 | 9,10-bis(phenylethynyl)anthracene | 20 mol % | — | NR |

[a]Reaction conditions: 0.5 mL of H$_2$O, 0.5 mL of methanol, 1 mmol of alkyne.
[b]GC yields, isolated yields in parentheses, an average of two runs.
[c]Temperature = 25° C.

But the most dramatic result is the acceleration obtained when one equivalent of a silver(I) salt is added as co-catalyst. This permits the rapid and quantitative formation of products while reducing catalyst loading from 10 mol % to 2 mol %. (Table 9)

TABLE 9

Effect of a silver salt on catalytic addition of water to alkynes.

| loading mol % | catalyst | time | yield[b] |
|---|---|---|---|
| 10 | (IPr)AuBr$_3$ | 24 h | 95% |
| 2 | (IPr)AuBr$_3$ + AgPF$_6$ | 1 h | 99% |
| 10 | AgPF$_6$ | 24 h | NR |

[a]Reaction conditions: 0.5 mL of H$_2$O, 0.5 mL of methanol, 1 mmol of phenylacetylene.
[b]GC yields, an average of two runs.

These initial catalytic observations raise many questions in term of mechanism of activation and nature of the true catalytic species. Ongoing studies in our laboratories are aimed at answering these questions.

We report the synthesis of the first series of well-defined (NHC)Au(III) complexes. Their straightforward synthesis can be carried out under aerobic conditions by oxidative addition of elemental bromine to the corresponding (NHC)Au(I) precursor. NMR and crystallographic data provide detailed information concerning the steric constraints and electronic effects produced by the different carbene environments around the Au(III) center. We also report the first use of a (NHC)Au(III) complex to catalyze an organic transformation. While the initial catalytic tests provide modest results, addition of a silver salt as a co-catalyst allowed the formation of a very efficient catalytic system. We are currently investigating the possible mechanism at play in this and related reactions.

EXPERIMENTAL SECTION

General Considerations. All reactions using (NHC)AuCl or (NHC)AuBr as starting material were carried out in air. All alkynes were used as received (Aldrich, Acros). All reactions were carried out open to air unless indicated otherwise. Solvents for NMR spectroscopy were dried over molecular sieves. NMR spectra were collected on a 500 or a 400 MHz Varian Gemini spectrometer. Flash chromatography was performed on silica gel (230-400 mesh) (Natland International Corporation). Elemental analyses were performed by Robertson Microlit Labs. (NHC)AuCl complexes were synthesized according to literature procedures.[26]

Synthesis of [(IPr)AuBr] (8): In a flask, (IPr)AuCl (1) (1.00 g, 1 equiv, 1.61 mmol) is dissolved in 5 mL of acetone with LiBr (1.19 g, 8.5 equiv, 13.70 mmol) and the solution is stirred at room temperature for 24 h. The acetone is removed by vacuum and 2 mL of DCM added to the residue. The organic phase is dried over MgSO$_4$ since LiBr is extremely hygroscopic. The solution is filtered over a plug of silica gel (3 g). After, reduction of the volume of DCM to 0.5 mL, 5 mL of pentane are added that lead to the appearance of a white precipitate. This precipitate is filtered, washed with 5 mL of cold pentane and dried to afford the desired complex. Yield: 0.94 g (87%). $^1$H NMR (CDCl$_3$): δ 7.50 (t, J=8.0 Hz, 2H, CH-aromatic), 7.28 (d, J=8.0 Hz, 4H, CH-aromatic), 7.17 (s, 2H, CH-imidazole), 2.56 (septet, J=7.0 Hz, 4H, CH(CH$_3$)$_2$), 1.34 (d, J=7.0 Hz, 12H, CH(CH$_3$)$_2$), 1.22 (d, J=7.0 Hz, 12H, CH(CH$_3$)$_2$); $^{13}$C NMR (CDCl$_3$): δ (ppm)=179.0 (s, C-carbene), 145.8 (s, CH-aromatic), 134.2 (s, CH-aromatic), 131.0 (s, CH-aromatic), 124.5 (s, CH-imidazole), 123.3 (s, CH-aromatic), 29.0 (s, CH(CH$_3$)$_2$), 24.7 (s, CH(CH$_3$)$_2$), 24.2 (s, CH(CH$_3$)$_2$). Elemental analysis calcd for C$_{27}$H$_{36}$N$_2$AuBr (665.21): C, 48.74; H, 5.41; N, 4.21. Found: C, 48.68; H, 5.17; N, 3.94.

Synthesis of [(IMes)AuBr] (9): A protocol similar to that used for 8 gave 9 (from 0.90 g, 1.68 mmol of 2) as a white solid. Yield: 0.780 g (80%). $^1$H NMR (CDCl$_3$): δ 7.09 (s, 2H, CH-imidazole), 6.98 (s, 4H, CH-aromatic), 2.33 (s, 6H, CH$_3$), 2.10 (s, 12H, CH$_3$); $^{13}$C NMR (CDCl$_3$): δ (ppm)=176.7 (s, C-carbene), 139.7 (s, CH-aromatic), 134.6 (s, CH-aromatic), 134.5 (s, CH-aromatic), 129.4 (s, CH-aromatic), 122.0 (s, CH-imidazole), 21.1 (s, CH$_3$), 17.7 (s, CH$_3$). Elemental analysis calcd for C$_{21}$H$_{24}$N$_2$AuBr (581.02): C, 43.39; H, 4.16; N, 4.82. Found: C, 43.51; H, 3.88; N, 4.66.

Synthesis of [(SIPr)AuBr] (10): In a flask (SIPr)AuCl (3) (1.00 g, 1 equiv, 1.61 mmol) is dissolved in 5 ml of acetone and LiBr (1.19 g, 8.5 equiv, 13.70 mmol) is added. This solution is stirred at room temperature for 48 h. The acetone is removed by vacuum and replaced by DCM. Solution is filtered over a plug of silica gel and dried over MgSO$_4$. After filtration and reduction of the volume of DCM to 0.5 mL, 5 mL of pentane were added until appearance of a white precipitate. This one is filtered, washed with pentane and dried out to afford the desired complex. It is worthy to note that washing the complex with water leads to its decomposition to the corresponding imidazolium salt. Yield: 0.610 g (57%). $^1$H NMR (CDCl$_3$): δ 7.41 (t, J=7.5 Hz, 2H, CH-aromatic), 7.23 (d, J=7.5 Hz, 4H, CH-aromatic), 4.04 (s, 4H, CH$_2$-imidazole), 3.05 (septet, J=6.5 Hz, 4H, CH(CH$_3$)$_2$), 1.41 (d, J=6.5 Hz, 12H, CH(CH$_3$)$_2$), 1.33 (d, J=6.5 Hz, 12H, CH(CH$_3$)$_2$); $^{13}$C NMR (CDCl$_3$): δ (ppm)=199.0 (s, C-carbene), 146.7 (s, CH-aromatic), 134.1 (s, CH-aromatic), 130.2 (s, CH-aromatic), 124.8 (s, CH-aromatic), 53.7 (s, CH$_2$-imidazole), 29.2 (s, CH(CH$_3$)$_2$), 25.3 (s, CH(CH$_3$)$_2$), 24.3 (s, CH(CH$_3$)$_2$). Elemental analysis calcd for C$_{27}$H$_{38}$N$_2$AuBr (667.14): C, 48.58; H, 5.74; N, 4.20. Found: C, 48.60; H, 5.60; N, 4.05.

Synthesis of [(SIMes)AuBr] (11): A protocol similar to that used for 10 provided 11 (from 1.00 g, 1.86 mmol of 4) as a white solid. Yield: 0.780 g (72%). $^1$H NMR (CDCl$_3$): δ 6.93 (s, 4H, CH-aromatic), 3.97 (s, 4H, CH$_2$-imidazole), 2.31 (s, 12H, CH$_3$), 2.29 (s, 6H, CH$_3$); $^{13}$C NMR (CDCl$_3$): δ (ppm)=198.1 (s, C-carbene), 139.1 (s, CH-aromatic), 135.7 (s, CH-aromatic), 134.7 (s, CH-aromatic), 130.0 (s, CH-aromatic), 50.9 (s, CH$_2$-imidazole), 21.3 (s, CH$_3$), 18.2 (s, CH$_3$). Elemental analysis calcd for C$_{21}$H$_{26}$N$_2$AuBr (583.08): C, 43.24; H, 4.49; N, 4.80. Found: C, 43.14; H, 4.22; N, 4.69.

Synthesis of [(ICy)AuBr] (12): A protocol similar to that used for 8 gave 12 (from 1.15 g, 2.47 mmol of 5) as a white solid. Yield: 0.980 g (78%). $^1$H NMR (CDCl$_3$): δ 6.95 (s, 2H, CH-imidazole), 4.57 (m, 2H, NCH-cyclohexyl), 2.07 (m, 4H, CH$_2$), 1.86 (m, 4H, CH$_2$), 1.73 (m, 2H, CH$_2$), 1.56 (m, 4H, CH$_2$), 1.43 (m, 4H, CH$_2$), 1.22 (m, 2H, CH); $^{13}$C NMR (CDCl$_3$): δ (ppm)=172.1 (s, C-carbene), 117.3 (s, CH-imidazole), 61.0 (s, NCH-cyclohexyl), 34.3 (s, CH$_2$), 25.5 (s, CH$_2$), 25.3 (s, CH$_2$). Elemental analysis calcd for C$_{15}$H$_{24}$N$_2$AuBr (509.20): C, 35.38; H, 4.75; N, 5.50. Found: C, 35.50; H, 4.73; N, 5.30.

Synthesis of [(IAd)AuBr] (13): A protocol similar to that used for 8 gave 13 (from 1.00 g, 1.76 mmol of 6) as a white solid. Yield: 0.590 g (55%). $^1$H NMR (CDCl$_3$): δ 7.08 (s, 2H, CH-imidazole), 2.56 (m, 14H, CH$_2$-adamantyl), 2.26 (m, 6H, CH$_2$-adamantyl), 1.75 (m, 10H, CH$_2$-adamantyl); $^{13}$C NMR (CDCl$_3$): δ (ppm)=170.2 (C-carbene), 115.2 (s, CH-imidazole), 59.2 (s, NCH-adamantyl), 44.0 (s, CH$_2$), 35.7 (s, CH$_2$), 29.8 (s, CH$_2$). Elemental analysis calcd for C$_{23}$H$_{32}$N$_2$AuBr (613.10): C, 45.04; H, 5.26; N, 4.57. Found: C, 44.97; H, 5.01; N, 4.44.

Synthesis of [(I$^t$Bu)AuBr]$^{7a}$ (14): A protocol similar to that used for 8 gave 14 (from 1.00 g, 2.42 mmol of 7) as a white solid. Yield: 0.810 g (73%). $^1$H NMR (CDCl$_3$): δ 7.09 (s, 2H, CH-imidazole), 1.87 (s, 18H, C(CH$_3$)$_3$); $^{13}$C NMR (CDCl$_3$): δ (ppm)=172.4 (s, C-carbene), 116.4 (s, CH-imidazole), 59.2 (s, C(CH$_3$)$_3$), 31.9 (s, C(CH$_3$)$_3$).

Synthesis of [(IPr)AuBr$_3$] (15): In a flask (IPr)AuBr (8) (0.840 g, 1 equiv, 1.262 mmol) is dissolved in 5 mL of DCM with bromine (0.240 g, 1.2 equiv, 1.514 mmol). The solution is stirred at room temperature for 1 hour. The volume of DCM is reduced to 0.5 mL by vacuum, removing at the same time the excess bromine. Then 5 mL of pentane is added to produce an orange precipitate. This solid is collected on a filter, washed with 5 mL of pentane and dried to afford the desired complex. Yield: 0.870 g (84%). $^1$H NMR (CDCl$_3$): δ 7.54 (t, J=7.5 Hz, 2H, CH-aromatic), 7.35 (d, J=7.5 Hz, 4H, CH-aromatic), 7.35 (s, 2H, CH-imidazole), 2.99 (septet, J=6.5 Hz, 4H, CH(CH$_3$)$_2$), 1.41 (d, J=6.5 Hz, 12H, CH(CH$_3$)$_2$), 1.13 (d, J=6.5 Hz, 12H, CH(CH$_3$)$_2$); $^{13}$C NMR (CDCl$_3$): δ (ppm)=146.2 (s, C-carbene), 145.8 (s, CH-aromatic), 132.6 (s, CH-aromatic), 131.6 (s, CH-aromatic), 126.1 (s, CH-aromatic), 124.7 (s, CH-imidazole), 29.1 (s, CH(CH$_3$)$_2$), 26.5 (s, CH(CH$_3$)$_2$), 23.0 (s, CH(CH$_3$)$_2$). Elemental analysis calcd for C$_{27}$H$_{36}$N$_2$AuBr$_3$ (825.27): C, 39.30; H, 4.40; N, 3.39. Found: C, 39.26; H, 4.12; N, 3.28.

Synthesis of [(IMes)AuBr$_3$] (16): In a flask (IMes)AuBr (9) (0.100 g, 1 equiv, 0.179 mmol) is dissolved in 1 mL of DCM and cooled to −78° C., then bromine (0.040 g, 1.2 equiv, 0.214 mmol) is added and the solution is stirred for 20 min. The excess bromine is removed by vacuum while the temperature is allowed to increase slowly to room temperature. Then 0.5 mL of DCM is added followed by 5 mL of pentane until the appearance of an orange precipitate. This suspension is filtered, the solid washed with pentane and dried to afford the desired complex. Yield: 0.120 g (94%). $^1$H NMR (CDCl$_3$): δ 7.32 (s, 2H, CH-imidazole), 7.06 (s, 4H, CH-aromatic), 2.37 (s, 6H, CH$_3$), 2.29 (s, 12H, CH$_3$); $^{13}$C NMR (CDCl$_3$): δ (ppm)=144.4 (s, C-carbene), 140.9 (s, CH-aromatic), 135.2 (s, CH-aromatic), 132.8 (s, CH-aromatic), 130.1 (s, CH-aromatic), 125.9 (s, CH$_2$-imidazole), 21.3 (s, CH$_3$), 19.7 (s, CH$_3$). Elemental analysis calcd for C$_{21}$H$_{24}$N$_2$AuBr$_3$ (740.82): C, 34.03; H, 3.26; N, 3.78. Found: C, 34.13; H, 3.49; N, 3.52.

Synthesis of [(SIPr)AuBr$_3$] (17): A protocol similar to that used for 15 gave 17 (from 0.280 g, 0.448 mmol of 10) as a orange solid. Yield: 0.360 g (97%). $^1$H NMR (CDCl$_3$): δ 7.43 (t, J=7.0 Hz, 2H, CH-aromatic), 7.26 (d, J=7.0 Hz, 4H, CH-aromatic), 4.29 (s, 4H, CH$_2$-imidazole), 3.41 (septet, J=6.5 Hz, 4H, CH(CH$_3$)$_2$), 1.46 (d, J=6.5 Hz, 12H, CH(CH$_3$)$_2$), 1.25 (d, J=6.5 Hz, 12H, CH(CH$_3$)$_2$); $^{13}$C NMR (CDCl$_3$): δ (ppm)=174.1 (s, C-carbene), 147.0 (s, CH-aromatic), 132.9 (s, CH-aromatic), 131.1 (s, CH-aromatic), 125.4 (s, CH-aromatic), 55.0 (s, CH$_2$-imidazole), 29.3 (s, CH(CH$_3$)$_2$), 27.4 (s, CH(CH$_3$)$_2$), 24.2 (s, CH(CH$_3$)$_2$). Elemental analysis calcd for C$_{27}$H$_{38}$N$_2$AuBr$_3$ (827.94): C, 39.20; H, 4.63; N, 3.39. Found: C, 39.52; H, 4.66; N, 3.32.

Synthesis of [(SIMes)AuBr$_3$] (18): A preparation similar to that used for 9 gave 18 (from 0.100 g, 0.185 mmol of 11) as a orange solid. Yield: 0.128 g (94%). $^1$H NMR (CDCl$_3$): δ 6.96 (s, 4H, CH-aromatic), 4.23 (s, 4H, CH$_2$-imidazole), 2.54 (s, 12H, CH$_3$), 2.31 (s, 6H, CH$_3$); $^{13}$C NMR (CDCl$_3$): δ (ppm)=172.3 (s, C-carbene), 140.1 (s, CH-aromatic), 135.8 (s, CH-aromatic), 132.1 (s, CH-aromatic), 130.3 (s, CH-aromatic), 53.3 (s, CH$_2$-imidazole), 21.2 (s, CH$_3$), 20.3 (s, CH$_3$). Elemental analysis calcd for C$_{21}$H$_{26}$N$_2$AuBr$_3$ (742.88): C, 33.94; H, 3.53; N, 3.77. Found: C, 34.19; H, 3.57; N, 3.66.

Synthesis of [(ICy)AuBr$_3$] (19): A protocol similar to that used for 15 gave 19 (from 0.365 g, 0.789 mmol of 12) as a yellow solid. Yield: 0.470 g (89%). $^1$H NMR (CDCl$_3$): δ 7.21 (s, 2H, CH-imidazole), 4.50 (m, 2H, NCH-cyclohexyl), 2.24 (m, 4H, CH$_2$), 1.90 (m, 4H, CH$_2$), 1.77 (m, 2H, CH$_2$), 1.51 (m, 4H, CH$_2$), 1.46 (m, 4H, CH$_2$), 1.21 (m, 2H, CH); $^{13}$C NMR (CDCl$_3$): δ (ppm)=136.8 (s, C-carbene), 120.5 (s, CH-imidazole), 61.1 (s, NCH-cyclohexyl), 33.4 (s, CH$_2$), 25.3 (s, CH$_2$), 25.1 (s, CH$_2$). Elemental analysis calcd for C$_{15}$H$_{24}$N$_2$AuBr$_3$ (668.82): C, 26.93; H, 3.63; N, 4.19. Found: C, 26.89; H, 3.56; N, 3.99.

Synthesis of [(IAd)AuBr$_3$] (20): A procedure similar to that used for 15 gave 20 (from 0.185 g, 0.325 mmol of 13) as a yellow solid. Yield: 0.240 g (95%). $^1$H NMR (CDCl$_3$): δ 7.53 (s, 2H, CH-imidazole), 2.57 (m, 14H, CH$_2$-adamantyl), 2.32 (m, 6H, CH$_2$-adamantyl), 1.75 (m, 10H, CH$_2$-adamantyl); $^{13}$C NMR (CDCl$_3$): δ (ppm)=132.9 (C-carbene), 121.4 (s, CH-imidazole), 63.8 (s, NCH-adamantyl), 44.1 (s, CH$_2$), 35.6 (s, CH$_2$), 30.2 (s, CH$_2$). Elemental analysis calcd for C$_{23}$H$_{32}$N$_2$AuBr$_3$ (778.93): C, 35.73; H, 4.17; N, 3.62. Found: C, 35.43; H, 4.05; N, 3.54.

Synthesis of [(I$^t$Bu)AuBr$_3$] (21): A protocol similar to that used for 15 gave 21 (from 0.360 g, 871 mmol of 14) as a yellow solid. Yield: 0.500 g (93%). $^1$H NMR (CDCl$_3$): δ 7.49 (s, 2H, CH-imidazole), 1.92 (s, 18H, C(CH$_3$)$_3$); $^{13}$C NMR (CDCl$_3$): δ (ppm)=134.2 (s, C-carbene), 122.7 (s, CH-imidazole), 62.6 (s, C(CH$_3$)$_3$), 32.2 (s, C(CH$_3$)$_3$). Elemental analysis calcd for C$_{11}$H$_{20}$N$_2$AuBr$_3$ (616.78): C, 21.41; H, 3.27; N, 4.54. Found: C, 21.59; H, 3.28; N, 4.47.

Screening of Substrates in Catalytic Addition of Water to Terminal Alkynes

Into a reaction vessel equipped with a magnetic stiffing bar and a reflux condenser were placed catalyst [(IPr)AuBr$_3$, 10 mol %, 83 mg] distilled water (0.5 mL), and methanol (5 mL). 1 mmol of the indicated alkyne was then added. The resulting mixture was refluxed and stirred using a magnetic plate in an oil bath for the indicated time. The reactions were monitored by gas chromatography. After reaching maximum conversion, the reaction mixture was allowed to cool to room temperature. Prior to workup, the reaction mixture was passed through a short silica column. The resulting filtrate was concentrated under reduced pressure and the residue diluted with methyl tert-butyl ether or diethyl ether and washed with brine. The ethereal solution was dried over magnesium sulfate. The solvent was then evaporated in vacuo. When necessary the product was purified by flash chromatography on silica gel with hexanes or 2-10% mixture of ethyl acetate in hexanes.

Isolated Products:

1-(4-Dimethylamino-phenyl)-ethanone[36] (Table 7, entry 1) The procedure afforded 133 mg (92%) of the product.

1-(4-Methoxy-phenyl)-ethanone[37] (Table 7, entry 2) The procedure afforded 118 mg (90%) of the product.

1-Phenyl-ethanone[38] (Table 7, entry 3) The procedure afforded 105 mg (88%) of the product.

(4-Acetyl-phenyl)-acetonitrile[39] (Table 7, entry 4) The procedure afforded 121 mg (86%) of the product.

1-Hydroxy-1,1-diphenyl-propan-2-one[40] (Table 7, entry 5) The procedure afforded 74 mg (36%) of the product.

1-(4-Chloro-phenyl)-ethanone[41] (Table 7, entry 6) The procedure afforded 118 mg (77%) of the product.

Cationic Gold(I) Complexes

A number of cationic gold(I) complexes have been synthesized and found to be stabilized by the use of N-heterocyclic carbene ligands. These species are often employed as in situ generated reactive intermediates in gold catalyzed organic transformations. An isolated, well-defined species was tested in gold-mediated carbene transfer reactions from ethyl diazoacetate.

As part of an ongoing program aimed at examining the role of N-heterocyclic carbenes (NHC) in transition metal-mediated reactions, we have recently studied the stabilizing effects of NHCs surrounding unsaturated and "reactive" metal centers. Since the isolation of the first free stable NHC, bearing two sterically demanding adamantyl groups on the nitrogens of an imidazolyl framework, by Arduengo,[42] sterically encumbering NHCs have allowed for the isolation of unusual 3-coordinate (NHC)Ni(CO)$_2$ complexes,[43] highly unsaturated 14 electron Ir(I) species,[44] a number of orthometallated ruthenium[45] and iridium[46] species, well-defined monomeric copper(I) species[47] and formally 16 electron second generation ruthenium-based olefin metathesis catalysts.[48] In view of the steric and electronic properties of this ligand class, the NHCs have been employed to prepare efficient and robust catalysts for transformations such as palladium-catalyzed cross-coupling reactions,[49] platinum-mediated hydrosilation,[50] palladium telomerization of butadiene and methanol,[51] copper-catalyzed hydrosilylation[52] and ruthenium-based olefin metathesis,[53] to name a few.

We recently became involved in the synthesis and isolation of well-defined (NHC)gold(I) complexes.[54] The first NHC gold(I) complexes were reported in 1989[55] and these usually bore two strongly bound ligands arranged in a linear fashion around a gold cation. These can be neutral or cationic and have the [(NHC)AuX][54] or [(NHC)$_2$Au$^+$][X$^-$][56] composition. Until recently, catalytic organogold chemistry appeared to have been somewhat forgotten. The "noble" character of the metal was possibly at the origin of the misconception that it would perform poorly in catalysis. This misconception has now been shattered as numerous examples of gold-phosphines[57] and gold-NHC[58] mediated transformations have recently appeared. Gold(I) halide complexes are especially efficient at activating alkyne moieties toward nucleophilic addition under mild reaction conditions.[57,58] A recent example by He also shows these complexes to be excellent co-catalysts in intra and intermolecular hydroamination of unsaturated olefins.[59] The use of silver salts, with an accompanying non-coordinating anion, is usually required to generate the active catalyst. It is commonly accepted that silver assists in halide abstraction from the gold center generating a highly electrophilic monoligated cationic gold complex.[60] While Echavarren has reported the isolation of a monoligated complex with a very bulky phosphine [(2-(di-t-butylphosphino)biphenyl)Au$^+$(CH$_3$CN)][SbPF$_6^-$] as an active catalyst for cycloisomerization,[60] attempts to synthesize or isolate I$^t$BuAuBF$_4$ by Baker[61] and PPh$_3$AuPF$_6$ by Gagosz[62] have so far failed due the rapid decomposition of these complexes to colloidal gold(0). In this communication, we report the isolation and characterization of such complexes by using a NHC ligand of sufficient bulk and a weakly coordinating solvent such as acetonitrile or THF leading to relatively stable yet reactive cationic gold(I) complexes.

The previously reported IPrAuCl[54] (IPr=1,3-bis(diisopropylphenyl)imidazol-2-ylidene), IMesAuCl[54] (IMes=1,3-bis (2,4,6-trimethylphenyl)imidazol-2-ylidene) and I$^t$BuAuCl[61] (I$^t$Bu=1,3-di-t-butylimidazol-2-ylidene) were dissolved in acetonitrile and AgPF$_6$ or AgBF$_4$, was added in stoichiometric amount leading to the rapid formation of a precipitate AgCl. After stirring the solutions for one minute, the suspensions were filtered through celite to give the novel complexes in solution (Scheme 3).[63] Appearance of colloidal gold(0) was noticeable after a few hours for all solutions. Attempts to obtain solid materials Scheme 3 synthesis route to catitonic NHC-Au(I) complexes.

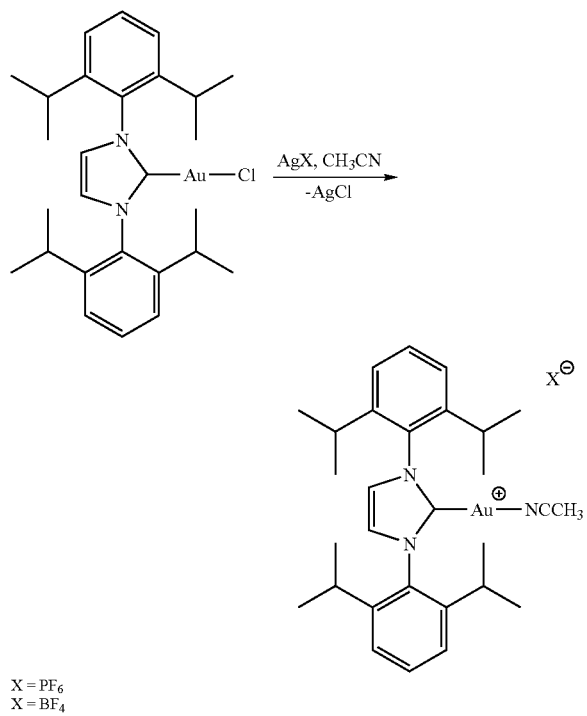

X = PF$_6$
X = BF$_4$ for all complexes by simply removing the solvent under vacuum only led to rapid decomposition of the materials obvious as white material turns to a greyish powder. Carrying out these reactions in the presence or absence of oxygen neither improved nor decreased the stability of the complexes.

Under these synthetic conditions, $^{42}$H and $^{54}$C NMR spectra of the neutral precursors and the novel products were recorded. While the pattern of the $^{42}$H NMR spectra remained the same with no trace of decomposition products between neutral and expected complexes, we observed a slight downfield shift for the backbone protons of the imidazole fragment. We attribute this change to a loss of electronic density in the aromatic heterocyclic system, due a delocalization of the n-electrons toward the more acidic gold centre. Moreover the $^{54}$C NMR spectra present signals for the carbenic carbons that are significantly shifted upfield for all complexes. Once again, this observation confirms a more acidic gold center.[61] Both $^{42}$H and $^{54}$C NMR studies support the presence of an electron deficient gold centre, confirming the very likely presence of monoligated gold(I) complexes.

We were interested in further testing the stability of such complexes. Attempts to synthesize the complexes in dichloromethane (DCM) or chloroform lead to the rapid appearance of large amounts of colloidal gold. The $^{42}$H NMR spectra of these reactions indicate the existence of two different NHC environments attributed to at least two NHC-gold species in solution. We confirmed in this manner the necessity of a coordinating solvent to stabilize the cationic gold centre. Ample precedents exist for coordinating solvent stabilization in Pt and Pd complexes.[64,65] Tetrahydrofuran (THF) was employed as an alternative to acetonitrile to generate IPrAu (S)PF$_6$ (S=coordinating solvent). In THF, no decomposition was observed even after 24 h in solution in air, but surprisingly a gel was obtained, attributed to the ring opening polymerization of THF.[66] The $^{54}$C NMR spectrum indicated a gold species in THF that is even more acidic than in acetonitrile with a carbenic carbon appearing at a more upfield position ($\delta$=159.7 ppm vs 167.6 ppm in CD$_3$CN). The complex in THF also displayed a second, more downfield, signal with a low intensity (after a few hours) for the deuterated THF that confirmed the formation of poly-THF.[66] It is worthy of note that the cationic polymerization of THF by ring opening, in the presence of a Lewis acid such as FeCl$_3$ or the trityl cation is well known.[67] In the present case, this polymerization behaviour confirms the presence of a cationic gold centered complex capable of acting as a Lewis acid, an interesting reaction profile we are presently examining. We also noticed that adding IPrAu(S)PF$_6$, synthesized from acetonitrile, into THF led to THF polymerization. While the acetonitrile needs to be displaced by the THF to initiate its polymerization, this result shows that in solution the molecules of solvent are weakly bound, labile and can be easily displaced from gold.

To unambiguously establish the solid state structure of one of these complexes, X-ray quality crystals suitable for single crystal diffraction studies were grown from a saturated acetonitrile solution of IPrAu(CH$_3$CN)PF$_6$ (22).[68] While the complex slowly decomposes over hours in solution, with appearance of colloidal gold(0), suitable X-ray quality crystals could be grown in this manner. It is noteworthy that the appearance of decomposition in solution or in the solid state for these complexes is related to the nature of the carbene and of the counter ion used. Complex 22 is the most stable complex observed so far.

Results from the diffraction study confirm the NMR determined structure and coordination of one acetonitrile to the gold centre. (FIG. 6). Metrical parameters reveal a nearly linear NHC—Au—NCCH$_3$ arrangement with a C—Au—N angle of 177.9(78)°. The C—Au bond distance (1.952(2) Å) is similar to that found for IPrAuCl[54]. The N—Au bond distance is 2.022(2) Å in the range of reported gold complexes with nitrogen donor ligands,[69] but slightly longer than known gold(I) complexes with coordinated acetonitrile such as [Au$^+$(MeCN)$_{x=2}$][X$^-$][70] with a Au—N distance bond equal to 1.96 Å. Finally, the N≡C bond distances between coordinated and non coordinated molecules of acetonitrile remain the same with a value equal to 1.12(3) Å[71] and explains the observed lability of the bound acetonitrile molecule.

Previous work form our laboratories has shown a very interesting catalytic behaviour of the complex IPrAuCl in the presence of NaBAr$_4$ (BAr$_4$=tetrakis(3,5-bis(trifluoromethyl) phenyl)borate) for the decomposition of ethyl diazoacetate (N$_2$=CHCO$_2$Et) and the subsequent transfer of the :CHCO$_2$Et unit to organic substrates.[58] This procedure has led to the functionalization of aromatic sp$^2$ and primary sp$^2$ C—H bonds of alkanes in moderate to high yields in a process that requires the assistance of the halide scavenger. Attempts to fully characterize a well-defined complex with the BAr$_4$ counterion has proven yet unsuccessful. Therefore, the availability of 22, in solution or as an isolated solid, now allows for the study of its catalytic properties toward this transformation. In reactions with catalytic amounts of 22, ethyl diazoacetate was reacted with several substrates (Table 10). In the case of good nucleophiles such as alcohols, quantitative conversion was obtained within minutes. Longer times were required for aniline whereas for t-butylamine incomplete conversion was observed even after 24 h. A similar result was found with styrene, for which three days were required for complete conversion into cyclopropanes. This trend could be attributed to the ease of replacement of the coordinated acetonitrile in 22 by the substrate. In accord with this, the use of more weakly coordinating molecules such benzene or 2,3- dimethylbenzene has led to undetectable yields: only very minor amounts of diethyl fumarate and maleate were detected by GC after several days, with most of the initial EDA remaining in the solution. But an additional experiment strongly suggests that this coordination of the substrate is not the only factor at play. The use of an equimolar mixture of IPrAuCl and NaBAr$_4$ as the catalyst in the reaction of styrene and EDA with a five-fold excess of CH$_3$CN added did not affect the course of the reaction, and led to the same mixture of products found in the absence of nitrile. We strongly suspect at this point that the counterion plays an important role in this catalytic transformation, a feature that is currently under investigation.

TABLE 10

Reaction of ethyl diazoacetate and several substrates in the presence of IPrAu(NCMe)PF$_6$ (1) as catalyst.[†]

| Substrate | Product | Time[a] | Yield[b] |
|---|---|---|---|
| Methanol | CH$_3$OCH$_2$CO$_2$Et | 0.2 | >99 |
| Ethanol | CH$_3$CH$_2$OCH$_2$CO$_2$Et | 0.2 | >99 |
| Aniline | PhN(H)CH$_2$CO$_2$Et | 24 | >99 |
| t-butylamine | t-BuN(H)CH$_2$CO$_2$Et | 24 | 55 |
| styrene | Cyclopropanes | 120 | >99 |
| benzene | no reaction[c] | 120 | — |
| 2,3-dimethylbutane | no reaction[c] | 120 | — |

[a]In hours:
[b]Determined by GC, diethyl fumarate and maleate accounted for 100%.
[c]EDA not consumed.

In conclusion, we have isolated and characterized by NMR spectroscopy and for one example by X-ray diffraction study well-defined cationic (NHC)Au(I)(S)X complexes which are postulated as the active pre-catalysts in numerous gold mediated organic transformations. The well-defined, isolated species IPrAu(NCMe)PF$_6$ (22) has been tested as the catalyst for the carbene transfer reaction from ethyl diazoacetate. The results suggest a large effect of the counterion in this transformation, when compared with the already reported in situ generated IPrAuCl+NaBAr$_4$ system.[58] Studies aimed at exploring this relative stability issue as well as investigations focusing on the reactivity of (NHC)Au complexes in organic chemistry are presently ongoing in our laboratories.

Supporting Information Available: Crystallographic information files (CIF) of the complexes (8) and (15-21) have been deposited with the CCDC, 12 Union Road, Cambridge, CB2 1EZ, U.K., and can be obtained on request free of charge, by quoting the publication citation ("Synthesis, Characterization and Reactivity of N-Heterocyclic Carbene Gold(III) Complexes." *Organometallics*, 2007, 26, 1376-1385) and deposition numbers 621434-621442. This material is also available free of charge via the Internet at http://pubs.acs.org.

Electronic supplementary information (ESI) available: Detailed experimental details with full NMR characterization data, catalytic procedures and crystallographic information file (CIF) for 22 deposited with the CCDC, 12 Union Road, Cambridge, CB2 1EZ, U.K. under the number: 296436.

[1](a) Teles, J. H.; Brode, S.; Chabanas, M. *Angew. Chem., Int. Ed.* 1998, 37, 1415-1418. (b) Nieto-Oberhuber, C.; Muñoz, M. P.; Buñuel, E.; Nevado, C.; Cárdenas, D. J.; Echavarren, A. M. *Angew. Chem., Int. Ed.* 2004, 43, 2402-2406. (c) Kennedy-Smith, J. J.; Staben, S. T.; Toste, F. D. *J. Am. Chem. Soc.* 2004, 126, 4526-4527. (d) Luzung, M. R.; Markham, J. P.; Toste, F. D. *J. Am. Chem. Soc.* 2004, 126, 10858-10859. (e) Johansson, M. J.; Gorin, D. J.; Staben, S. T.; Toste, F. D. *J. Am. Chem. Soc.* 2005, 127, 18002-18003. (f) Gorin, D. J.; Davis, N. R.; Toste, F. D. *J. Am. Chem. Soc.* 2005, 127, 11260-11261. (g) Fructos, M. R.; de Frémont, P.; Nolan, S. P.; Díaz-Requejo, M. M.; Pérez, P. J. *Organometallics* 2006, 25, 2237-2241.

[2](a) Zhang, L.; Kozmin, S. A. *J. Am. Chem. Soc.* 2004, 126, 11806-11807. (b) Marion, N.; de Frémont, P.; Lemière, G.; Stevens, E. D.; Fensterbank, L.; Malacria, M.; Nolan, S. P. *Chem. Commun.* 2006, 19, 2048-2050. (c) Nieto-Oberhuber, C.; Lopez, S.; Muñoz, M. P.; Jímenez-Núñez, E.; Buñuel, E.; Cárdenas, D. J.; Echavarren, A. M. *Chem. Eur. J.* 2006, 12, 1694-1702. (d) Jímenez-Núñez, E.; Claverie, C. K.; Nieto-Oberhuber, C.; Echavarren, A. M. *Angew. Chem., Int. Ed.* 2006, 45, 5452-5455. (e) Sun, J.; Conley, M. P.; Zhang, L.; Kozmin, S. A. *J. Am. Chem. Soc.* 2006, 128, 9705-9710. (f) Dubé, P.; Toste, F. D. *J. Am. Chem. Soc.* 2006, 128, 12062-12063.

[3](a) Fructos, M. R.; Belderrain, T. R.; de Frémont, P.; Scott, N. M.; Nolan, S. P.; Díaz-Requejo, M. M.; Pérez, P. J. *Angew. Chem., Int. Ed.* 2005, 44, 5284-5288.

[4]Marion, N.; Díez-González, S.; de Frémont, P.; Noble, A. R.; Nolan, S. P. *Angew. Chem., Int. Ed.* 2006, 45, 3647-3650.

[5]Guan, B.; Xing, D.; Cai, G.; Wan, X.; Yu, N.; Fang, Z.; Yang, L.; Shi, Z. *J. Am. Chem. Soc.* 2005, 127, 18004-18005.

[6]Ito, H.; Yajima, T.; Tateiwa, J.; Hosomi, A. *Chem. Commun.* 2000, 981-982.

[7](a) Baker, M. V.; Barnard. P. J.; Brayshaw, S. K.; Hickey, J. L.; Skelton B. W.; White, A. H. *Dalton Trans.* 2005, 1, 37-43. (b) Mézailles, N.; Ricard, L.; Gagosz, F. *Org. Lett.* 2005, 7, 4133-4136. (c) Ferrer, C.; Echavarren, A. M. *Angew. Chem., Int. Ed.* 2006, 45, 1105-1109. (d) de Frémont, P.; Stevens, E. D.; Fructos, M. R.; Díaz-Requejo, M. M.; Pérez, P. J.; Nolan, S. P. *Chem. Commun.* 2006, 2045-2047. (e) Belting, V.; Krause, N. *Org. Lett.* 2006, 8, 4489-4492. (f) Hashmi, A. S. K.; Blanco, C.; Kurpejovic, E.; Frey, W.; Bats, J. W. *Adv. Synth. Cat.* 2006, 348, 709-713.

[8](a) Muir, J. A.; Muir, M. M.; Pulgar, L. B. *Acta. Cryst.* 1985, C41, 1174-1176. (b) King, C.; Khan, M. N. L.; Staples, R. J.; Fackler, J. P. Jr. *Inorg. Chem.* 1992, 31, 3236-3238. (c) Müller, T. E.; Green, J. C.; Mingos, D. M. P.; McPartlin, C. M.; Whittingham, C.; Williams, D. J.; Woodroffe, T. M. *J. Organomet. Chem.* 1998, 551, 313-330. (d) Raubenheimer, H. G.; Esterhuysen, M. W.; Timoshkin, A.; Chen, Y.; Frenking, G. *Organometallics* 2002, 21, 3173-3181. (e) Stefanescu, D. M.; Yuen, H. F.; Glueck, D. S.; Golen, J. A.; Zakharov, L. N.; Incarvito, C. D.; Rheingold, A. L. *Inorg. Chem.* 2003, 42, 8891-8901. (f) Reiter, S. A.; Nogai, S. D.; Schmidbaur, H. *Dalton Trans.* 2005, 247-255.

[9](a) Cetinkaya, B.; Dixneuf, P. Lappert, M. F. *J. C. S. Dalton Trans.* 1974, 1827-1833. (b) Raubenheimer, H. G.; Lindeque, L.; Cronje, S. *J. Organomet. Chem.* 1996, 511, 177-184. (c) Wang, H. M. J.; Chen, C. Y. L.; Lin, I. J. B. *Organometallics* 1999, 18, 1216-1223. (d) Vicente, J.; Chicote, M.-T.; Abrisqueta, M. D.; Alvarez-Falcón, M. M.; Ramírez de Arellano, M. C.; Jones, P. G. *Organometallics* 2003, 22, 4327-4333. (e) Wang, H. M. J.; Vasam, C. S.; Tsai, T. Y. R.; Chen, S.-H.; Chang, A. H. H.; Lin, I. J. B. *Organometallics* 2005, 24, 486-493. (f) Barnard, P. J.; Baker, M. V.; Berners-Price, S. J.; Skelton, B. W.; White, A. H. *Dalton Trans.* 2004, 1038-1047. (g) Lin, I. J. B.; Vasam, C. S. *Can. J. Chem.* 2005, 83, 812-825. (h) Wang, J.-W.; Li, Q.-S.; Xu, F.-B.; Song, H.-B.; Zhang, Z.-Z. *Eur. J. Org. Chem.* 2006, 1310-1316.

[10]Bonati, F.; Burini, A.; Pietroni, B. R.; Bovio, B. *J. Organomet. Chem.* 1991, 408, 271-280.

[11]Nishina, N.; Yamamoto, Y. *Angew. Chem., Int. Ed.* 2006, 45, 3314-3317.

[12]Sato, K.; Asao, N.; Yamamoto, Y. *J. Org. Chem.* 2005, 70, 8977-8981.

[13] Shi, Z.; He, C. J. Org. Chem. 2004, 69, 3669-3671.

[14] (a) Morita, N.; Krause, N. Org. Lett. 2004, 6, 4121-4123. (b) Kim, N.; Kim, Y.; Park, W.; Sung, D.; Gupta, A. K.; Oh, C. H. Org. Lett. 2005, 7, 5289-5291. (c) Antoniotti, S.; Genin, E.; Michelet, V. Geñet, J.-P. J. Am. Chem. Soc. 2005, 127, 9976-9977. (d) Barluenga, J.; Diéguez, A.; Fernández, A.; Rodríguez, F.; Fañanás, F. J. Angew. Chem., Int. Ed. 2006, 45, 2091-2093. (e) Liu, J.; Muth, E.; Flörke, U.; Henkel, G.; Merz, K.; Sauvageau, J.; Schwake, E.; Dyker, G. Adv. Synth. Catal. 2006, 348, 456-462.

[15] (a) Li, Z.; Shi, Z.; He, C. J. Organomet. Chem. 2005, 690, 5049-5054. (b) Nair, V.; Vidya, N.; Abhilash, G. Tetrahedron Lett. 2006, 47, 2871-2873.

[16] (a) Hashmi, A. S. K.; Frost, T. M.; Bats, J. W. Org. Lett. 2001, 3, 3769-3771. (b) Diker, G.; Hildebrandt, D.; Liu, J.; Merz, K. Angew. Chem., Int. Ed. 2003, 42, 4399-4402. (c) Wei, C.; Li, C.-J. J. Am. Chem. Soc. 2003, 125, 9584-9585. (d) Yao, T.; Zhang, X.; Larock, R. C. J. Am. Chem. Soc. 2004, 126, 11164-11165. (e) Yao, X.; Li, C.-J. J. Am. Chem. Soc. 2004, 126, 6884-6885. (f) Shi, Z.; He, C. J. Am. Chem. Soc. 2004, 126, 13596-13597. (g) Hashmi, A. S. K.; Schwarz, L.; Rubenbauer, P.; Blanco, M. C. Adv. Synth. Catal. 2006, 348, 705-708. (h) Fürstner, A.; Hannen, P. Chem. Eur. J. 2006, 12, 3006-3019.

[17] (a) Casado, R.; Contel, M.; Laguna, M.; Romero, P.; Sanz, S. J. Am. Chem. Soc. 2003, 125, 11925-11935. (b) Hashmi, A. S. K.; Weyrauch, J. P.; Rudolph, M.; Kurpejovic, E. Angew. Chem., Int. Ed. 2004, 45, 6545-6547. (c) González-Arellano, C.; Corma, A.; Iglesias, M.; Sánchez, F. Chem. Commun. 2005, 27, 3451-3453. (d) Lo, V. K.-Y.; Liu, Y.; Wong, M.-K.; Che, C.-M. Org. Lett. 2006, 8, 1529-1532.

[18] (a) Duckworth, V. F.; Stephenson, N. C. Inorg. Chem. 1969, 8, 1661-1664. (b) Uson, R.; Laguna, A.; Buil, J. J. Organomet. Chem. 1975, 85, 403-408. (c) Godfrey, S. M.; Ho, N.; McAuliffe, C. A.; Pritchard, R. G. Angew. Chem., Int. Ed. 1996, 35, 2344-2346.

[19] Vicente, J.; Arcas, A.; Mora, M.; Solans, X.; Font-Altaba. M. J. Organomet. Chem. 1986, 309, 369-378.

[20] (a) Komiya, S.; Shibue, A. Organometallics 1985, 4, 684-687. (b) Komiya, S.; Ishikawa, M.; Ozaki, S. Organometallics 1988, 7, 2238-2239. (c) Blanco, M. C; Fernández, E. J.; Olmos, M. E.; Pérez, J. Organometallics 2004, 23, 4373-4381.

[21] (a) Minghetti, G.; Bonati, F. J. Organomet. Chem. 1973, 54, C62-C63. (b) Minghetti, G.; Bonati, F. J. Organomet. Chem. 1974, 73, C43-C44. (c) Manojlović-Muir, L. J. Organomet. Chem. 1974, 73, C45-C46. (d) Usón, R.; Laguna, A.; Brun, P.; Laguna, M.; Abad, M. J. Organomet. Chem. 1981, 218, 265-273.

[22] (a) Schneider, D.; Schier, A.; Schmidbaur, H. Dalton Trans. 2004, 1995-2005. (b) Schneider, D.; Schuster, O.; Schmidbaur, H. Dalton Trans. 2005, 1940-1947.

[23] Welhan, M.; Thiel, R.; Fuchs, J.; Beck, W.; Fehlhammer, W. P. J. Organomet. Chem. 2000, 613, 159-169.

[24] (a) Raubenheimer, H. G.; Olivier, P. J.; Lindeque, L.; Desmet, M.; Hrusak, J.; Kruger, G. J. J. Organomet. Chem. 1997, 544, 91-100. (b) Kühlkamp, P.; Raubenheimer, H. G.; Field, J. S.; Desmet, M. J. Organomet. Chem. 1998, 552, 69-74.

[25] Schmidbaur, H. Gold, Progress in Chemistry, Biochemistry and Technology, John Wiley & Sons Ltd: West Sussex, England, 1999, p: 358.

[26] de Frémont, P.; Scott, N. M.; Stevens, E. D.; Nolan, S. P. Organometallics 2005, 24, 2411-2418.

[27] Herrmann, W. A.; Runte, O.; Artus, G. J. Organomet. Chem. 1995, 501, C1-C4.

[28] (a) Wang, H. M. J.; Chen, C. Y. L.; Lin, I. J. B. Organometallics 1999, 18, 1216-1223. (b) Vicente, J.; Chicote, M.-T.; Abrisqueta, M. D.; Alvarez-Falcón, M. M.; Ramirez de Arellano, M. C.; Jones, P. G. Organometallics 2003, 22, 4327-4333. (c) de Frémont, P.; Stevens, E. D.; Eelman, M. D.; Fogg, D. E.; Nolan, S. P. Organometallics 2006, in press.

[29] Beurskens, P. T.; Blaauw, H. J. A.; Cras, J. A.; Steggerda, J. J. Inorg. Chem. 1968, 7, 805-810.

[30] White-Morris, R. L.; Olmstead, M. M.; Jiang, F.; Tinti, D. S.; Balch, A. L. J. Am. Chem. Soc. 2002, 124, 2327-2336.

[31] de Frémont, P.; Scott, N. M.; Stevens, E. D.; Ramnial, T.; Lightbody, O. C.; MacDonald, C. L. B.; Clyburne, J. A. C.; Abernethy, C. D.; Nolan, S. P. Organometallics 2005, 24, 6301-6309.

[32] (a) Cinellu, M. A.; Minghetti, G.; Pinna, M. V.; Stoccoro, S.; Zucca, A.; Manassero, M. J. Chem. Soc., Dalton Trans. 1999, 2823-2831. (b) Wile, B. M.; Burford, R. J.; McDonald, R.; Ferguson, M. J.; Stradiotto, M. Organometallics 2006, 25, 1028-1035.

[33] (a) Burawoy, A.; Gibson, C. S.; Hampson, G. C.; Powell, H. M. J. Chem. Soc. 1937, 2, 1690-1695. (b) Perutz, M. F.; Weisz, O. J. Chem. Soc. (London) 1946, 438-442. (c) Lörcher, K. P.; Strähle, J. Z. Naturforsch. B: Anorg. Chem., Org. Chem. 1975, 30, 662-664. (d) Fabretti, A. C.; Giusti, A.; Malavasi, W. J. Chem. Soc. Dalton Trans. 1990, 3091-3093.

[34] Pyykkö, P.; Tamm, T. Organometallics 1998, 17, 4842-4852.

[35] Schneider, S. K.; Herrmann, W. A; Herdtweck, E. Z. Anorg. Allg. Chem. 2003, 629, 2363-2370.

[36] Klingsberg, E.; Schreiber, A. M., J. Am. Chem. Soc. 1962, 84, 2941-2944.

[37] Cacchi, S.; Fabrizi, G.; Gavazza, F.; Goggiamani, A. Org. Lett. 2003, 5, 289-291.

[38] The product is commercially available and the spectra of the isolated product were compared with spectra from a sample obtained from Aldrich.

[39] Wu, L.; Hartwig, J. F. J. Am. Chem. Soc. 2005, 127, 15824-15832.

[40] Hou, Z.; Takamine, K.; Aoki, O.; Shiraishi, H.; Fujiwara, Y.; Taniguchi H. J. Org. Chem. 1988, 53, 6077-6084.

[41] Murphy, J. A.; Commeureuc, A. G. J.; Snaddon, T. N.; McGuire, T. M.; Khan, T. A.; Hisler, K.; Dewis, M. L.; Carling, R. Org. Lett. 2005, 7, 1427-1429.

[42] A. J. III. Arduengo, R. L. Harlow and M. Kline, J. Am. Chem. Soc., 1991, 113, 361-363.

[43] R. Dorta, E. D. Stevens, C. D. Hoff and S. P. Nolan, J. Am. Chem. Soc., 2003, 125, 10490-10491.

[44] N. M. Scott, R. Dorta, E. D. Stevens, A. Correa, L. Cavallo and S. P. Nolan, J. Am. Chem. Soc., 2005, 127, 3516-3526.

[45] R. F. R. Jazzar, M. Varrone, A. D. Burrows, S. A. McGregor, M. F. Mahon and M. K. Whittlesey, Inorg. Chim. Acta, 2006, 359, 815-820.

[46] R. Dorta, E. D. Stevens and S. P. Nolan, J. Am. Chem. Soc., 2004, 126, 5054-5055.

[47] H. Kaur, F. Kauer-Zinn, E. D. Stevens and S. P. Nolan, Organometallics, 2004, 23, 1157-1160.

[48] J. Huang, E. D. Stevens and S. P. Nolan, J. Am. Chem. Soc., 1999, 121, 2674-2678.

[49] M. S. Viciu, R. F. Germaneau, O, Navarro-Fernández, E. D. Stevens and S. P. Nolan, Organometallics, 2002, 21, 5470-5472; O. Navarro, N. Marion, N. M. Scott, J. González, D. Amoroso, A. Bell and S. P. Nolan, Tetrahedron, 2005, 61, 9716-9722.

[50] J. W. Sprengers, M. J. Maayke, M. A. Duin, J. C. Kingsley and J. C. Elsevier, J. Organomet. Chem., 2003, 679, 149-

152; O. Busine, G. Berthon-Gelloz, J.-F. Briere, S. Sterin, G. Mignani, P. Branlard, B. Tinant, J.-P. Declercq and E. I. Marko, *Chem. Commun.*, 2005, 30, 3856-3858.

[51] R. Jackstell, S. Harkal, H. Jiao, A. Spannenberg, C. Borgmann, D. Roettger, F. Nierlich, M. Elliot, S. Niven, K. Cavell, O, Navarro, M. S. Viciu, S. P. Nolan and M. Beller, *Chem. Eur. J.*, 2004, 10, 3891-3900.

[52] S. Diez-González, H. Kaun, F. K. Zinn, E. D. Stevens and S. P. Nolan, *J. Org. Chem.*, 2005, 70, 4784-4796.

[53] L. Jafarpour, H.-J. Schanz, E. D. Stevens and S. P. Nolan, *Organometallics*, 1999, 18, 5416-5425; A. Fuerstner, O. R. Thiel, L. Ackermann, H.-J. Schanz and S. P. Nolan, *J. Org. Chem.*, 2000, 65, 2204-2207.

[54] P. de Frémont, N. M. Scott, E. D. Stevens and S. P. Nolan, *Organometallics*, 2005, 24, 2411-2418.

[55] F. Bonati, A. Burini, B. R. Pietroni and B. J. Bovio, *J. Organomet. Chem.*, 1989, 375, 147-160.

[56] H. M. K. Wang and I. J. B. Lin, *Organometallics*, 1998, 17, 972-975; P. J. Barnard, M. V. Baker, S. J. Berners-Price, B. W. Skelton and A. H. White, *Dalton Trans.*, 2004, 1038-1047.

[57] For recent example: L. Zhang and S. A. Kozmin, *J. Am. Chem. Soc.*, 2005, 127, 6962-6963; M. J. Johansson, D. J. Gorin, S. T. Staben and F. D. Toste, *J. Am. Chem. Soc.*, 2005, 127, 18002-18003.

[58] M. R. Fructos, T. R. Belderrain, P. de Frémont, N. M. Scott, S. P. Nolan, M. M. Díaz-Requejo and P. J. Pérez, *Angew. Chem. Int. Ed.*, 2005, 44, 5284-5288; N. Marion, S. Diez-González, P. de Frémont, A. R. Noble and S. P. Nolan, Submitted for publication.

[59] J. Zhang, C.-G. Yang and C. He, *J. Am. Chem. Soc.*, 2006, ASAP article

[60] C. Ferrer and A. M. Echavarren, *Angew. Chem. Int. Ed.*, 2006, 45, 1105-1109.

[61] M. V. Baker, P. J. Barnard. S. K. Brayshaw, J. L. Hickey. B. W. Skelton and A. H. White, *Dalton Trans.*, 2005, 1, 37-43. The existence of a cationic species such as [NHCAu(NCCH$_3$)]Cl cannot be excluded at this point and counterion and solvent effects are presently being examined.

[62] N. Mézaille, L. Ricard and F. Gagosz, *Org. Let.*, 2005, 7, 4133-4136.

[63] In a scintillation vial, in air, (NHC)AuCl (1 eq.) is dissolved in 2 mL of acetonitrile and AgX (1 eq.) is added. The reaction is stirred one minute and filtered over celite to give a colorless solution. Complete removal of the solvent under vacuum leads to the isolation of a white powder that rapidly decomposes (turning grey or purple). Slow solvent evaporation leads to formation of crystals of the desired product. [(IPrAu)$^+$(CH$_3$CN)][PF$_6^-$] (1): $^1$H NMR (400 MHz, CD$_3$CN) δ 7.66 (s, 2H, CH-imidazole), 7.63 (t, J=8.0 Hz, 2H, CH-aromatic), 7.45 (d, J=8.0 Hz, 2H, CH-aromatic), 2.51 (sept, J=6.8 Hz, 2H, CH(CH$_3$)$_2$), 1.31 (d, J=6.8 Hz, 12H, CH(CH$_3$)$_2$), 1.26 (d, J=6.8 Hz, 12H, CH(CH$_3$)$_2$). $^{13}$C NMR (100 MHz, CDCl$_3$) δ 167.6 (s, C-carbene), 148.1 (s, CH-aromatic), 135.4 (s, CH-aromatic), 132.3 (s, CH-aromatic), 127.4 (s, CH-aromatic), 126.6 (s, CH-imidazole), 28.9 (s, CH(CH$_3$)$_2$), 23.9 (s, CH(CH$_3$)$_2$), 23.3 (s, CH(CH$_3$)$_2$).

[64] R. Bertani, R. A. Michelin, M. Mozzon, A. Sassi, M. Basato, A. Biffis, G. Martinati and Z. Zecca, *Inorg. Chem. Commun.*, 2001, 4, 281-284; R. Bertani, M. Biasioli, K. Darini, R. A. Michelin, M. Mozzon, F. Visentin and L. Zanotto, *J. Organomet. Chem.*, 2002, 642, 32-39.

[65] M. S. Viciu, F. Kauer-Zinn, E. D. Stevens and S. P. Nolan, *Organometallics*, 2003, 22, 3175-3177.

[66] S. Kobayashi, K. Morikawa and T. Saegusa, *Macromolecules*, 1975, 8, 954-956.

[67] I, Kuntz, *J. Pol. Sc., Part B: Pol. Let.*, 1966, 4, 427-430; V. M. Siderko, V. P. Mardykin, *USSR. Vestn. Beloruss. Univ.*, 1970, 2, 35-37.

[68] Crystal Data: (C$_{31}$H$_{42}$AuN$_4$)(PF$_6$), M=812.62, monoclinic, space group P2$_1$/n, a=8.9662(6), b=18.347(1), c=21.693(2) Å, β=96.841(1)°, V=3544.0(4) Å$^3$, T=298(2)K, Z=4., μ=4.254 mm$^{-1}$, 53909 reflections measured using a Bruker SMART 1K CCD diffractometer, 4626 unique (Rint=0.062), R1=0.0493 for all data.

[69] W. Conzelmann, W. Hiller and J. Strähle, *Z. Anorg. Allg. Chem.*, 1982, 485, 81-87; P. W. R. Corfield and H. M. M. Shearer, *Acta Crystallogr.*, 1967, 23, 156-162.

[70] D. M. P. Mingos and J. Yau, *J. Organomet. Chem.*, 1994, 479, C16-C17; S. Ahrland, K. Nilsson, I. Person, A. Yushi and J. E. Penner-Hahn, *Inorg. Chem.*, 1989, 28, 1833-1838.

[71] Two molecules of acetonitrile are present in the asymmetric unit cell. One is bound to the gold, the other is a solvent of co-crystallization.

For more information about the present invention, see the papers entitled "Synthesis, isolation and characterization of cationic gold(I) N-heterocyclic carbene (NHC) complexes" *Chem. Commun.*, 2006, 2045-2047, first published as an Advance Article on the web 10 Apr. 2006, and "Synthesis, Characterization and Reactivity of N-Heterocyclic Carbene Gold(III) Complexes." *Organometallics*, 2007, 26, 1376-1385, both attached to our U.S. Provisional Patent Application Ser. No. 60/910,385 and incorporated herein by reference. All of the notes and references in those papers are likewise incorporated herein by reference.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A stable complex of general formula [(NHC)M-L$_n$]$^+$X$_m^-$ where NHC is a carbene ligand; M is Au; L is a two electron donor ligand, n and m are 0 or 1, and X is a counteranion, where the carbene ligand is an N-heterocyclic carbene from the group consisting of imidazolyl-2-ylidene, imidazolidin-2-ylidene, tetrahydropyrimid-2-ylidene, thiazolium-based NHC, and triazolium-based NHC.

2. A stable complex of general formula [(NHC)AuX$_3$] where NHC is a carbene ligand; X is a halide or pseudohalide.

3. A complex of claim 2 where the carbene ligand is an N-heterocyclic carbene from the group consisting of imidazolyl-2-ylidene, imidazolidin-2-ylidene, tetrahydropyrimid-2-ylidene, thiazolium-based NHC, triazolium-based NHC.

4. A method of making a cationic complex of general formula [(NHC)M-L$_n$]$^+$X$_m^-$ where NHC is a carbene ligand; M is Au; L is a two electron donor ligand, n and m are 0 or 1, and X is a counteranion, comprising:

causing a (NHC)AuX complex to come into contact with a silver salt to remove the X on the neutral precursor in the presence of a coordinating solvent.

5. A method of making a neutral complex (NHC)AuX where NHC is a carbene ligand; and X is a counteranion, comprising: causing a (Me$_2$S)AuX complex to come into contact with a NHC in the presence of a solvent.

6. A method of making the neutral complex (NHC)AuX$_3$ of claim 2, comprising: causing a (NHC)AuX complex to come into contact with a halogen X$_2$ in the presence of a solvent.

7. The method of claim 6, wherein the halogen X$_2$ is from the group consisting of Cl$_2$, Br$_2$, and I$_2$.

8. The complex of general formula [(NHC)M-L$_n$]$^+$X$_m^-$ where NHC is a carbene ligand; M is Au; L is a two electron donor ligand, n and m are or 1, and X is a counteranion, where X is nothing and L=halide or pseudohalide with composition NHC—Au-L.

* * * * *